United States Patent [19]

Ellis et al.

[11] Patent Number: 4,826,876

[45] Date of Patent: May 2, 1989

[54] CHEMICAL COMPOUNDS HAVING SELECTIVE THYROMIMETIC ACTIVITY

[75] Inventors: David Ellis, Letchworth; John C. Emmett; Anthony H. Underwood, both of Welwyn; Paul D. Leeson, Cambridge, all of England

[73] Assignee: Smith Kline & French Laboratories Limited, Welwyn Garden City, England

[21] Appl. No.: 136,240

[22] Filed: Dec. 21, 1987

Related U.S. Application Data

[63] Continuation of Ser. No. 818,626, Jan. 14, 1986, Pat. No. 4,766,121.

[30] Foreign Application Priority Data

Jan. 18, 1985 [GB] United Kingdom ............... 8501372

[51] Int. Cl.$^4$ .................... C07C 101/72; A61K 31/24
[52] U.S. Cl. ..................... 514/535; 514/539; 514/544; 514/546; 514/558; 514/562; 514/563; 514/564; 514/568; 514/571; 514/616; 514/618; 514/619; 514/620; 514/622; 558/29; 558/30; 558/32; 558/33; 560/9; 560/18; 560/21; 560/36; 560/40; 560/45; 560/46; 560/55; 560/57; 560/64; 560/65; 560/66; 560/105; 560/138; 560/140; 562/426; 562/432; 562/435; 562/441; 562/447; 562/452; 562/453; 562/468; 562/465; 562/473; 562/474; 564/153; 564/154; 564/155; 564/157; 564/158; 564/162; 564/166; 564/167
[58] Field of Search ............... 560/9, 18, 21, 36, 40, 560/45, 46, 55, 57, 64, 65, 66, 105, 138, 140; 562/426, 432, 435, 441, 447, 452, 453, 468, 465, 473, 474; 564/153, 154, 155, 157, 158, 162, 166, 167; 514/539, 544, 546, 558, 562, 563, 564, 568, 571, 616, 618, 619, 620, 622, 535

[56] References Cited

U.S. PATENT DOCUMENTS

| | | | |
|---|---|---|---|
| 3,017,428 | 1/1962 | Jorgansen | 560/40 |
| 3,410,891 | 11/1968 | Hughes | 560/40 |
| 3,477,954 | 11/1969 | Reynolds, et al. | 514/567 |

OTHER PUBLICATIONS

Asher, N. L., *Current Therapeutic Res.*, vol. 14, No. 8, pp. 525–539 (Aug. 1972).
The Coronary Drug Project, *JAMA*, vol. 220, No. 7, pp. 996–1008 (May 1972).
Goldfine, I. D., et al., "Activities of Thyroid Hormones and Related Compounds in an In Vitro Thymocyte Assay", *J. Biol. Chem.*, vol. 251, No. 14, pp. 4233–4238 (1976).
Simon, Z. et al., "Studiu Structura Chimica–Activitate Biologica Pentru Situsul Fixator de Tiroxina al Prealbuminei Umane", *Timisoara Med.*, vol. 26, No. 3, pp. 26–28 (1981).
Gwinup, G. et al., *Am. J. Med. Sci.*, vol. 254, pp. 416–420 (Oct. 1967).
Gharib, H., et al., "Radioimmunoassay for Triiodothyronine ($T_3$): U, Affinity and Specificity of the Antibody for $T_3$", *J. Clin. Endocrinol. Metab.*, vol. 33, No. 3, pp. 509–516 (Sep. 1971).
Ahmad, P., et al., "Parachors in Drug Design", *Biochem. Pharm.*, vol. 24, No. 10, pp. 1103–1109 (1975).
Korener, D., et al., "Binding of Selected Iodothyronine Analogues to Receptor Cites of Isolated Rat Hepatic Nuclei", *J. Biol. Chem.*, vol. 250, No. 16, pp. 6417–6423 (1975).
Andrea, T. A., et al., "Binding of Thyroid Hormones and Analogues to the Human Plasma Protein Prealbumin", *Biochemistry*, vol. 19, pp. 55–63 (1980).
Dietrich, S. W., et al., "Thyroxine Analogues, 23 Quantitative Structure-Activity Correlation Studies of In Vivo and In Vitro Thyromimetic Activities", *Journal of Medicinal Chemistry*, vol. 20, No. 7, pp. 863–880 (Jul. 1977).
Jorgensen, E. C., et al., "The Nature of the Thyroid Hormone Receptor", *Int. Congr. Ser.-Excepta Med.*, 378, Thyroid Res. pp. 303–6 (1976).

*Primary Examiner*—Michael L. Shippen
*Attorney, Agent, or Firm*—Nancy S. Mayer; Stuart R. Suter; Alan D. Lourie

[57] ABSTRACT

This invention relates to chemical compounds which have selective thyromimetic activity. A compound of this invention is 3,5-dibromo-3'-[6-oxo-3(1H)-pyridazinyl-methyl]-thyronine.

10 Claims, No Drawings

CHEMICAL COMPOUNDS HAVING SELECTIVE THYROMIMETIC ACTIVITY

This is a continuation of application Ser. No. 818,626 filed Jan. 14, 1986, now U.S. Pat. No. 4,766,121.

The present invention relates to novel chemical compounds, intermediates useful in their preparation, pharmaceutical compositions containing them and a method of producing thyromimetic effects in certain tissues except the heart.

The naturally occurring thyroid hormones, 3,5,3'-triiodo-L-thyronine ($T_3$) and 3,5,3',5'-tetraiodo-L-thyronine ($T_4$) are used in replacement therapy in cases of thyroid deficiency in man.

In addition, thyroid hormones and thyromimetic analogues thereof have been given to individuals with a view to treating other conditions (Burrow, G. N., "Thyroid Hormone Therapy in non-Thyroid Disorders", The Thyroid, Eds Werner, S. C. and Ingbar, S. H., 4th Edition, Harper and Row, 1978, 974). For example, $T_3$ and $T_4$ have been used in the treatment of obesity (Gwinup, G., and Poucher, R. Am. J. Med. Sci., 254, 416, 1976, Asher, W. L., Current Therapeutic Res. 14, 525, 1972) and $T_4$ and certain thyromimetics have been shown to lower serum cholesterol concentrations in atherosclerotic patients (The Coronary Drug Project Research Group, JAMA, 220, 996, 1972). However, the direct cardiac effects encountered at doses greater than those used in replacement therapy have restricted the widespread use of thyroid hormones and thyromimetic analogues thereof as therapeutic agents.

The compounds of the present invention are structurally related to $T_3$ and $T_4$ and have been found to exhibit selective thyromimetic activity. When administered to test animals, they mimic the effects of thyroid hormones in certain tissues at doses which have little or no direct thyromimetic activity on the heart. The present invention therefore provides, in a first aspect, a compound of structure (I)

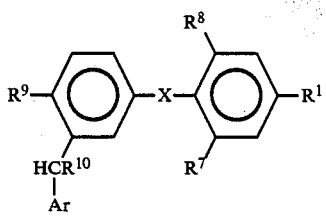

in which,
$R^1$ is —$CH_2CR^2R^3NR^4R^5$ or $YCOR^6$;
$R^2$ is hydrogen or $C_{1-4}$alkyl;
$R^3$ is hydrogen or —$COR^6$;
$R^4$ is hydrogen or $C_{1-4}$alkyl;
$R^5$ is hydrogen, $C_{1-4}$alkyl or $C_{1-4}$alkanoyl;
$R^6$ is hydroxy, $C_{1-4}$alkoxy, or —$NR^4R^5$;
Y is a bond or $C_{1-4}$alkylene;
$R^7$ and $R^8$ are the same or different and are each hydrogen, halogen, $C_{1-4}$alkyl, nitro or amino;
X is oxygen, sulphur, or $CH_2$;
$R^9$ is hydroxy or a bioprecursor thereof;
$R^{10}$ is hydrogen or $C_{1-4}$alkyl; and
Ar is 4-hydroxyphenyl, 5-hydroxy-2-pyridyl, 6-oxo-3(1H)-pyridyl or a 6-oxo-3(1H)-pyridazinyl group,
or a pharmaceutically acceptable salt thereof.

Suitably $R^3$ is hydrogen; preferably $R^3$ is $COR^6$. Suitably $R^4$ is $C_{1-4}$alkyl and $R^5$ is hydrogen, $C_{1-4}$ alkyl or $C_{1-4}$alkanoyl; preferably $R^4$ and $R^5$ are both hydrogen. Suitably $R^6$ is $C_{1-4}$alkoxy or $NR^4R^5$; preferably $R^6$ is hydroxy.

Suitably Y is a bond. Preferably Y is $C_{1-4}$alkylene; most preferably Y is methylene, propylene or butylene.

Suitably $R^7$ and $R^8$ are the same or different and are each hydrogen, nitro or amino. Preferably $R^7$ and $R^8$ are both $C_{1-4}$alkyl; most preferably $R^7$ and $R^8$ are the same and are each halogen.

Suitably X is $CH_2$. Preferably X is sulphur; most preferably X is oxygen.

Suitably $R^9$ is a bioprecursor of a hydroxy group for example, $C_{1-4}$alkoxy, aryl $C_{1-4}$alkoxy (for example $OCH_2Ph$), $C_{1-4}$alkanoyloxy (for example $OCOCH_3$), aryl$C_{1-4}$alkanoyloxy (for example $OCOCH_2Ph$), arylsulphonyloxy (for example toluene sulphonyloxy), alkylsulphonyloxy (for example methane sulphonyloxy), or O-glucuronide; preferably $R^9$ is hydroxy.

Suitably $R^{10}$ is $C_{1-4}$alkyl; preferably $R^{10}$ is hydrogen.

Suitably, Ar is a 4-hydroxyphenyl group or a 5-hydroxy-2-pyridyl group. Preferably Ar is a 6-oxo-3(1H)-pyridyl group; most preferably, Ar is a 6-oxo-3(1H)-pyridazinyl group.

$C_{1-4}$alkyl groups either alone or as part of another group, for example, $C_{1-4}$alkoxy or $C_{1-4}$alkanoyl are methyl, ethyl, propyl or butyl; preferably, methyl or ethyl.

Halogen atoms are bromine, chlorine or iodine; preferably bromine or iodine.

Compounds of structure (I) can be obtained in the form of a racemic or diastereomeric mixture or as individual isomers or mixtures thereof. For example, in compounds of structure (I) in which $R^2$ is hydrogen and $R^3$ is —$COR^6$, the group $R^1$ is an amino acid residue of structure

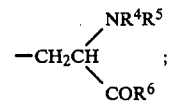

compounds of structure (I) having such a group $R^1$ can exist in the form of the D-isomer, L-isomer or DL-mixture of isomers. Suitably, such compounds of structure (I) are provided as the DL mixture of isomers; preferably they are provided as the D-isomer or L-isomer substantially free of the other isomer.

The present invention includes all isomeric forms in resolved and unresolved states of the compounds of structure (I).

Particular compounds of structure (I) include those in which $R^1$ is a group

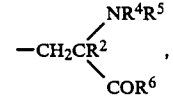

$R^7$ and $R^8$ are both halogen, $R^9$ is hydroxy, $R^{10}$ is hydrogen and Ar is 6-oxo-3-(1H)-pyridyl or 6-oxo-3(1H)-pyridazinyl, for example:
3,5-diiodo-3'-[6-oxo-3(1H)-pyridylmethyl]thyronine,
3,5-dibromo-3'-[6-oxo-3(1H)-pyridylmethyl]thyronine,
3,5-dichloro-3'-[6-oxo-3(1H)-pyridylmethyl]thyronine,
3,5-diiodo-3'-[6-oxo-3(1H)-pyridazinylmethyl]thyronine, 3,5-dibromo-3'-[6-oxo-3(1H)-pyridazinylmethyl]thyronine,
3,5-dichloro-3'-[6-oxo-3(1H)-pyridazinylmethyl]thyronine,
4-(4'-hydroxy-3'-(6-oxo-3(1H)-pyridylmethyl)phenylthio)-3,5-diiodophenylalanine,
4-(4'-hydroxy-3'-(6-oxo-3(1H)-pyridylmethyl)phenylthio)3,5-dibromophenylalanine;
and the foregoing compounds in which the group $R^1$ is in the form of the L-isomer, for example:
L-3,5-diiodo-3'-[6-oxo-3(1H)-pyridylmethyl]thyronine,
L-3,5-dibromo-3'-[6-oxo-3(1H)-pyridylmethyl]thyronine,
L-3,5-dichloro-3'-[6-oxo-3(1H)-pyridylmethyl]thyronine,
L-3,5-diiodo-3'-[6-oxo-3(1H)-pyridazinylmethyl]thyronine,
L-3,5-dibromo-3'-[6-oxo-3(1H)-pyridazinylmethyl]thyronine,
L-3,5-dichloro-3'-[6-oxo-3(1H)-pyridazinylmethyl]thyronine.

Further examples of compounds of the present invention include:
3,5-diiodo-3'-[4-hydroxybenzyl]thyronine,
3,5-diiodo-3'-[5-hydroxy-2-pyridylmethyl]thyronine,
4-(4'-hydroxy-3'-(4-hydroxybenzyl)-phenylthio)3,5-diiodophenylalanine,
3,5-dibromo-3'-[6-oxo-3(1H)-pyridylmethyl]thyronine ethyl ester,
3,5-dibromo-3'-[6-oxo-3(1H)-pyridylmethyl]thyroninamide,
3,5-diiodo-3'-(6-oxo-3(1H)-pyridylmethyl)thyropentanoic acid,
3,5-dibromo-3'-(6-oxo-3(1H)-pyridylmethyl)thyroethanoic acid,
3,5-diiodo-3'-(6-oxo-3(1H)-pyridylmethyl)-thyrobutanoic acid,
3,5-dimethyl-3'-[6-oxo-3(1H)-pyridylmethyl]thyronine.
N-acetyl-3,5-diiodo-3'(6-oxo-3(1H)-pyridylmethyl)-thyronine,
3,5-dibromo-3'-(6-oxo-3(1H)-pyridylmethyl)thyropropanoic acid.

Compounds of structure (I) in which $R^4$ and $R^5$ are the same or different and are each hydrogen or $C_{1-4}$alkyl can form acid addition salts with for example, hydrochloric, hydrobromic, hydroiodic, methanesulphonic, or sulphonic acids. Acid addition salts can also be formed with the group Ar when it is a nitrogen containing heterocycle. Compounds of structure (I) in which $R^6$ and/or $R^9$ are OH can form salts with metal ions such as alkali metals, for example sodium or potassium or alkaline earth metals for example calcium or magnesium. Further, any carboxy group present can be optionally salified. The ability to form acid addition and/or metal salts will be subject to the nature of the relevant compounds as will be readily understood by the skilled person.

In addition, it will be appreciated that under appropriate pH conditions, compounds of structure (1) in which $R^1$ is

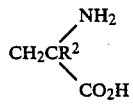

may exist as zwitterions. The present invention includes all such zwitterionic forms of the compounds of structure (I). Similarly, the present invention includes compounds of structure (I) in which the group Ar is in the zwitterionic form.

The present invention also includes the compounds of structure (I) in which the group Ar is in an alternative tautomeric form. For example, where Ar is 6-oxo-3(1H)-pyridyl, the present invention includes the tautomeric form thereof, wherein Ar is (6-hydroxy-3-pyridyl) group; similarly, where Ar is 6-oxo-3(1H)-pyridazinyl, the present invention includes the tautomeric form thereof wherein Ar is a 6-hydroxy-3-pyridazinyl group.

A process for the preparation of a compound of structure (I) or a pharmaceutically acceptable salt thereof, comprises deprotection of a compound of structure (II)

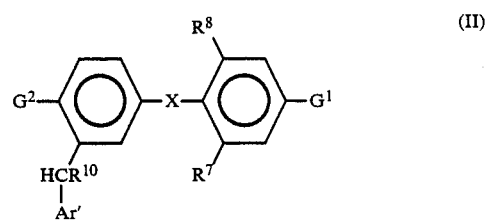

in which
$G^1$ is a protected group $R^1$;
$R^7$, $R^8$, $R^{10}$ and X are as defined for structure (I);
$G^2$ is hydroxy or a protected hydroxy group; and
Ar' is 6-oxo-3(1H)-pyridyl, 6-oxo-3(1H)-pyridazinyl or a protected group Ar;
and thereafter, if necessary, forming a pharmaceutically acceptable salt.

The term "protected group $R^1$" refers to a group $R^1$ as defined for structure (I) in which any primary or secondary amine groups are in protected form, and in which any hydroxy groups are, where appropriate, in protected form. For example, suitable protected groups $R^1$ include those of structure

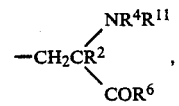

wherein $R^6$ is hydroxy, $C_{1-4}$alkoxy or $NR^4R^{11}$, $R^4$ is hydrogen or $C_{1-4}$alkyl and $R^{11}$ is $C_{1-4}$alkanoyl, trifluoroacetyl, aryl $C_{1-4}$alkanoyl, $C_{1-4}$alkoxycarbonyl, aryl $C_{1-4}$alkoxycarbonyl or phthalamido. Preferably, $R^4$ is hydrogen, $R^{11}$ is trifluoroacetyl and $R^6$ is methoxy. Other suitable protected groups $R^1$ include those of structure

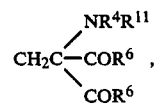

wherein $R^4$ and $R^{11}$ are as hereinbefore defined and $R^6$ is $C_{1-4}$alkoxy. Suitable protected groups $R^1$ of structure $YCOR^6$ include those wherein $R^6$ is $C_{1-4}$alkoxy. Other suitable protecting groups are as described in "Amino Acids, Peptides and Proteins" Specialist Periodical Reports, Royal Society of Chemistry, 1969, and succeeding years.

Suitable protected hydroxy groups $G^2$ include for example, $C_{1-4}$alkoxy, aryl $C_{1-4}$alkoxy (for example, $OCH_2Ph$), $OC_{1-4}$alkanoyl (for example $OCOCH_3$), $OC_{1-4}$alkanoyl aryl (for example $CO_2CH_2Ph$), arylsulphonyloxy (for example toluene sulphonyloxy), or alkylsulphonyloxy (for example methane sulphonyloxy); preferably $C_{1-4}$ alkoxy, for example methoxy. Other suitable protecting groups are described in "Protective Groups in Organic Synthesis", Greene, T. W., John Wiley & Sons, 1981, 87.

The term protected group Ar refers to a group Ar in which the oxygen function is in protected form, for example a group of structure:

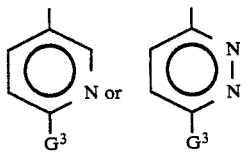

wherein $G^3$ is $C_{1-4}$alkoxy, aryloxy, aryl$C_{1-4}$alkoxy, chloro or bromo; or a group of structure,

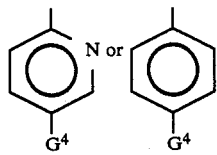

wherein $G^4$ is $C_{1-4}$alkoxy, aryloxy or aryl$C_{1-4}$alkoxy.

Suitably $G^3$ is aryloxy, (for example phenoxy) or aryl $C_{1-4}$alkoxy, (for example benzyloxy). Preferably $G^3$ is $C_{1-4}$ alkoxy, (for example, methoxy), or halogen (for example, chloro or bromo).

Suitably $G^4$ is aryl $C_{1-4}$alkoxy (for example benzyloxy), or aryloxy (for example phenoxy). Preferably $G^4$ is $C_{1-4}$alkoxy (for example, methoxy).

Deprotection of protected groups in $G^1$, $G^2$ and Ar' of structure (II) can be achieved by standard methods depending on the precise nature of the protecting groups to be removed.

In general, protected hydroxy groups $G^2$ are preferably methoxy groups which can be removed by treatment with boron tribromide in dichloromethane or hydrogen bromide in acetic acid.

In general, protected groups $R^1$ of structure

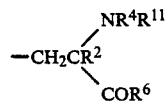

are preferably those in which $R^4$ is hydrogen, $R^{11}$ is trifluoroacetyl and $R^6$ is methoxy. Such groups $R^{11}$ and $R^6$ can be deprotected by treatment with hydrogen bromide or hydrogen chloride in acetic acid, or aqueous sodium hydroxide in ethanol.

In general, protected groups Ar are preferably those in which $G^3$ is methoxy or halogen, for example chlorine, and $G^4$ is methoxy. Deprotection of protected groups Ar in which $G^3$ or $G^4$ are methoxy to the corresponding groups Ar can be achieved by treatment with boron tribromide in dichloromethane. Deprotection of protected groups Ar in which $G^3$ is chlorine can be achieved by treatment with sodium acetate in acetic acid.

The sequence of deprotection steps depends on the choice of protecting groups; for example, (1) compounds of structure (II) in which $G^1$ is a protected group $R^1$ in which $R^4$ is hydrogen, $R^{11}$ is trifluoroacetyl and $R^6$ is methoxy, $G^2$ is methoxy and Ar' is a protected group Ar in which $G^3$ or $G^4$ is methoxy can be deprotected by treatment first with boron tribromide in dichloromethane to deprotect the protected group Ar and convert $G^2$ to a hydroxy group, and then with hydrochloric acid in acetic acid to deprotect the protected group $R^1$; and (2) compounds of structure (II) in which $G^1$ and $G^2$ are as described in (1) above and Ar' is a protected group Ar in which $G^3$ is chlorine for example 6-chloropyridazine, can first be treated with sodium acetate in acetic acid to deprotect the group Ar to form the corresponding 6-oxo-3(1H)-pyridazine, and then boron tribromide in dichloromethane to convert $G^2$ to a hydroxy group, and finally sodium hydroxide to deprotect the protected group $R^1$.

Alternative reagents, combinations of protecting groups and order or reactions will be apparent to those skilled in the art.

Alternatively, a process for the preparation of a compound of structure (I) or a pharmaceutically acceptable salt thereof comprises (a) reaction of a compound of structure (III)

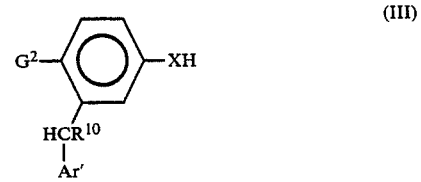

in which $R^{10}$ and Ar' are as defined for structure (II), X is oxygen or sulphur, and $G^2$ is a protected phenolic hydroxy group with a compound of structure (IV)

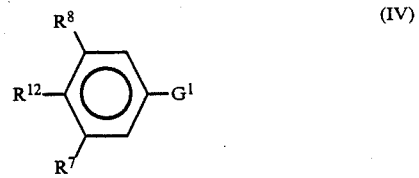

wherein $G^1$ is CHO, CN, $CH_2Hal$, a group $R^1$ or a protected group $R^1$, $R^{12}$ is halogen or hydroxy, one of $R^7$ and $R^8$ is nitro and the other is bromo or nitro and Hal is halogen;

(b) reaction of a compound of structure (V)

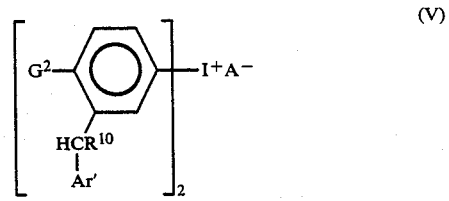

in which $G^2$ and $R^{10}$ are as defined for structure (III), Ar' is a protected group Ar and $A^-$ is an anion of a strong acid, with a compound of structure (IVA)

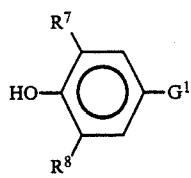
(IVA)

wherein $G^1$ is as described for structure (IV) and $R^7$ and $R^8$ are the same or different and each may be hydrogen, halogen, $C_{1-4}$alkyl or nitro;

(c) reaction of a compound or structure (VA)

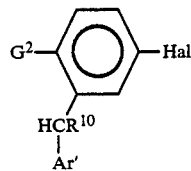
(VA)

wherein $R^{10}$ and $G^2$ are as defined for structure (III) Ar' is a protected group Ar and Hal is halogen, with a compound of structure (IVC)

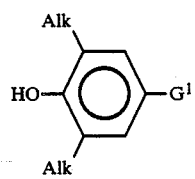
(IVC)

wherein Alk is $C_{1-4}$alkyl and $G^1$ is as defined for structure (IV);

(d) reaction of a compound of structure (III) with a compound of structure (IVD)

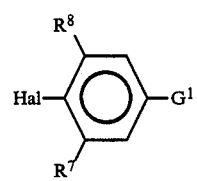
(IVD)

in which Hal is halogen, $G^1$ is $NO_2$ or CN and $R^7$ and $R^8$ are the same or different and are each hydrogen, halogen or $C_{1-4}$alkyl;

(e) reaction of a compound of structure (VI)

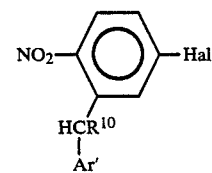
(VI)

in which Ar' is a protected group Ar, $R^{10}$ is as defined for structure (III) and Hal is halogen, with a compound of structure (IVE)

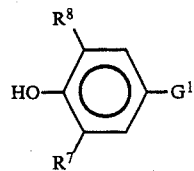
(IVE)

in which $G^1$ is as described for structure (IV) and $R^7$ and $R^8$ are the same or different and each is hydrogen, halogen or $C_{1-4}$alkyl;

(f) reaction of a compound of structure (VI) with a compound of structure (IVF)

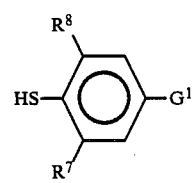
(IVF)

in which $R^7$ and $R^8$ are the same or different and each is hydrogen or $C_{1-4}$alkyl and $G^1$ is as defined for structure (IV);

(g) reaction of a compound of structure (VII)

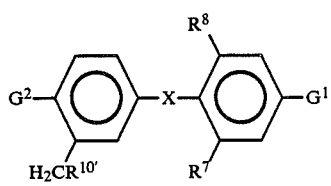
(VII)

in which $G^1$ is $NO_2$, CHO, CN, $CH_2Hal$, a group $R^1$ or a protected group $R^1$, Hal is halogen; $G^2$ is hydroxy, or a protected hydroxy group, $R^{10'}$ is CN, CHO or $CO_2C_{1-4}$alkyl and X, $R^7$ and $R^8$ are as described for structure (II), with a compound of structure (VIII) or a compound of structure (IX)

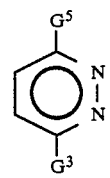
(VIII)

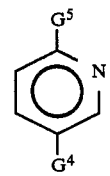
(IX)

in which $G^3$ and $G^4$ are as hereinbefore described and $G^5$ is chloro or bromo; (h) reacting a compound of structure (X)

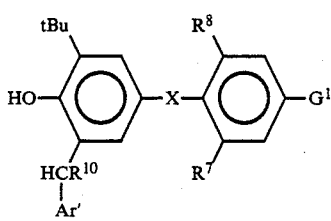

(X)

in which $G^1$ is a protected group $R^1$; $R^7$ and $R^8$ are the same or different and are each hydrogen or halogen; X is oxygen or sulphur, $R^{10}$ is hydrogen or $C_{1-4}$alkyl and Ar' is 6-oxo-3(1H)-pyridyl, 6-oxo-3(1H)-pyridazinyl or a protected group Ar, with an acid, and thereafter, if necessary, (i) converting a group $G^1$ to a group $R^1$ or protected group $R^1$;

(ii) converting a group $G^2$ to a hydroxy group or a protected hydroxy group;

(iii) converting a group $R^{10'}$ to a group $R^{10}$;

(iv) converting a group $R^7$ or $R^8$ into another group $R^7$ or $R^8$;

(v) removing any protecting groups;

(vi) forming a pharmaceutically acceptable salt.

The reaction of a compound of structure (III) with a compound of structure (IV) in which $R^7$ and $R^8$ are both $NO_2$ and $R^{12}$ is hydroxy can be carried out in an organic solvent in the presence of an alkyl or aralkyl sulphonyl chloride, for example, methane sulphonyl chloride or toluene sulphonyl chloride. Preferably the reaction is carried out under reflux in pyridine as a solvent in the presence of methane sulphonyl chloride. The reaction of a compound of structure (III) with a compound of structure (IV) in which $R^{12}$ is halogen can be carried out by heating in a suitable organic solvent for example dichloromethane or methylethyl ketone, preferably in the presence of a base, for example, potassium carbonate.

Compounds of structure (III) in which Ar' is a protected group Ar can be prepared from compounds of structure (IIIA)

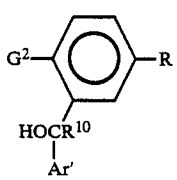

(IIIA)

in which R is hydrogen or a protected hydroxy group susceptible to selective removal in the presence of the protected group $G^2$, for example $OCH_2Ph$, Ar' is a protected group Ar, and $G^2$ and $R^{10}$ are as defined for structure (III). Suitable reaction steps include for example, where in structure (III) X is oxygen and Ar' is a protected group Ar, acylation of a compound of structure (IIIA) wherein R is $OCH_2Ph$ followed by hydrogenolysis.

Compounds of structure (IIIA) can themselves be prepared from compounds of structure (IIIB):

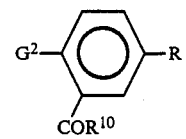

(IIIB)

in which R is hydroxy or a protected hydroxy group susceptible to selective removal in the presence of a protected group $G^2$, and $G^2$ and $R^{10}$ are as defined for structure (IIIA); for example, by reaction of a compound of structure (IIIB) where R is H or a protected hydroxy group, with:

(i) a 2-alkoxy-5-halo-pyridine in the presence of n-butyl lithium to give a compound of the structure (IIIA) in which Ar' is 6-alkoxy-3-pyridine;

(ii) a 5-alkoxy-2-halopyridine in the presence of n-butyl lithium to give a compound of structure (IIIA) in which Ar' is 5-alkoxy-2-pyridine; and (iii) a 4-alkoxy phenyl magnesium bromide, to give a compound of structure (IIIA) in which Ar' is 4-alkoxyphenyl.

Compounds of structure (III) in which X is oxygen and Ar' is a 6-oxo-3(1H)-pyridazinyl group can be prepared by reduction of a compound of structure (IIIB) in which R is a protected hydroxy group, with, for example, sodium borohydride, followed by reaction with phosphorus tribromide, sodium cyanide and then a compound of structure (VIII) for example 3,6-dichloropyridazine to give a compound of structure (IIIC)

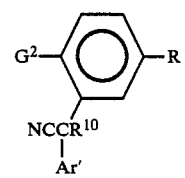

(IIIC)

in which R is a protected hydroxy group, $R^{10}$ and $G^2$ are as defined for structure (IIIA) and Ar' is 6-chloro-3-pyridazine. Acidic or basic hydrolysis of the compound of structure (IIIC) so formed with, for example, hydrochloric acid in acetic acid or, alternatively, sodium acetate in acetic acid followed by hydrochloric acid in acetic acid, and deprotection of the group R, gives a compound of structure (III) in which X is oxygen and Ar is a 6-oxo-3(1H)-pyridazinyl group.

Compounds of structure (III) in which Ar is 6-oxo-3(1H)-pyridyl can be prepared by conversion of compounds of structure (III) in which Ar is a 6-alkoxy-3-pyridyl group.

Compounds of structure (IIIB) in which R is for example $OCH_2Ph$ can be prepared by benzylation of compounds of structure (IIIB) where R is hydroxy.

Compounds of structure (IIIB), where R is hydroxy can be prepared by standard methods, for example as described by H. Ulrich et al, J. Org. Chem., 1974, 39, 2437.

Compounds of structure (III) in which X is sulphur can be prepared by reaction of a compound of structure (IIIA) in which R is hydrogen, with for example chlorine and lead thiocyanate or potassium thiocyanate in methanol, followed by triphenyl phosphine and aqueous acid.

Compounds of structure (IV) can be prepared by methods known in the art, for example as described in "Thyroid Hormones and Analogues. I. Synthesis, Physical Properties and Theoretical Calculations" E. C. Jorgensen, Hormonal Proteins and Peptides, Vol. VI, 1978, Academic Press, N.Y. and references cited therein.

The reaction of a compound of structure (IVA) with a compound of structure (V) can be carried out in an organic solvent in the presence of a base and a copper catalyst and, optionally in the presence of a crown ether. Suitable organic solvents include alcohols, for example methanol or ethanol, halogenated solvents for example dichloromethane or chloroform, dimethylformamide or dimethylsulphoxide. Preferably the reaction is carried out in dichloromethane as a solvent. Suitable bases include tertiary amines, for example triethylamine, and alkali metal hydrides or alkoxides, for example sodium hydride or potassium-t-butoxide. Preferably triethylamine or potassium-t-butoxide may be used as bases. Suitable copper catalysts include copper/bronze or copper I salts, for example, copper I benzoate or copper I halides. Preferably, the reaction is carried out in the presence of copper bronze. When the base is an alkali metal hydride or alkoxide, the reaction may be carried out in the presence of a crown ether. Preferably, the reaction can be carred out in the presence of 18-crown-6. The reaction is carried out preferably at ambient temperature. Hence, the reaction is preferably carried out in the presence of triethylamine or potassium-t-butoxide and copper bronze in dichloromethane as a solvent at ambient temperature, and, where the base is potassium-t-butoxide, optionally in the presence of 18-crown-6.

Suitably $A^{31}$ in structure (V) may be for example perchlorate, trifluoroacetate, halide or sulphate. Preferably $A^-$ is trifluoroacetate or perchlorate. The compound of structure (V) wherein $A^-$ is trifluoroacetate can be prepared by reaction of a compound of structure (IIIA) wherein R is hydrogen with iodine tris-trifluoroacetate in trifluoroacetic anhydride and trifluoroacetic acid. Treatment of the compound of structure (V) wherein $A^-$ is trifluoroacetate with aqueous sodium perchlorate affords the compound of structure (V) $A^-$ is perchlorate.

Compounds of structure (V) can be prepared from compounds of structure (IIIA) where R is hydrogen by standard methods for the preparation of iodonium salts, for example as described by G. F. Koser in "The Chemistry of Functional Groups, Supplement D., p. 1265, 1983, S. Patai and Z. Rappaport, Eds, John Wiley & Sons Ltd.

The reaction between compounds of structure (VA) and (IVC) can be carried out in the presence of a copper catalyst in an organic solvent at elevated temperature and, optionally, in the presence of a base. Preferably the reaction is carried out under reflux in pyridine in the presence of potassium carbonate and copper.

For the reaction of compounds of structure (III) and (IVD) when $G^1$ in (IVD) is nitro, the reaction can be carried out at elevated temperature in organic solvent in the presence of a base. Preferably the reaction is carried out under reflux in methyl ethyl ketone in the presence of potassium carbonate. When, in formula (IVD) $G^1$ is cyano, the reaction can be carried out in an organic solvent at elevated temperature in the presence of a base and optionally, a copper catalyst. Preferably the reaction is carried out at a temperature of 40°–50° in dimethylformamide as solvent in the presence of sodium hydride as base.

The reaction between compounds of structure (VI) and (IVE) can be carried out at elevated temperature in an organic solvent in the presence of a base.

Suitable organic solvents include, for example, dimethylformamide or dimethylsulphoxide. Suitable bases include for example sodium hydride, sodium methoxide or potassium carbonate. Suitably the reaction is carried out at a temperature of 100° to 140° in dimethylformamide in the presence of sodium hydride. Alternatively, the reaction can be carried out at a temperature of 90° to 140° in dimethylsulphoxide in the presence of sodium or potassium hydroxide using a procedure analogous to that described in Journal of Organic Chemistry, 1968, 33, 1245.

The reaction between compounds of structure (VI) and (IVF) can be carried out in the presence of a base in an organic solvent.

The reaction between compounds of structure (VII) and (VIII) or (IX) can be carried out under basic conditions in a suitable reaction solvent at temperatures between ambient and the reflux temperature of the solvent. For example suitable bases and solvents include sodium hydride in dimethylformamide, or potassium t-butoxide in dichloromethane, optionally in the presence of a crown ether. Other suitable bases and solvents will be apparent to those skilled in the art.

Compounds of structure (VII) can be prepared by procedures analogous to those known in the art, in particular using the reactions described in paragraphs (a) to (f) and (h) above.

The reaction between a compound of structure (X) and an acid is generally carried out in a solvent at elevated temperature. The acid must be capable of removing the t-butyl group, for example, a Lewis Acid such as aluminium trichloride, or hydrobromic acid. Suitably the reaction is carried out in an organic solvent, for example toluene, anisole or N,N-dimethylaniline, optionally in the presence of a co-solvent such as nitromethane. Preferably the reaction is carried out in toluene and nitromethane in the presence of aluminium trichloride; or in acetic acid in the presence of hydrobromic acid.

Compound of structure (X) are prepared from compounds of structure (XA)

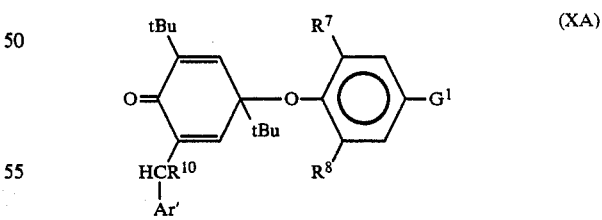

in which $G_1$, $R^7$, $R^8$, $R^{10}$ and Ar' are as described for structure (X) by treatment with a Lewis acid to remove the t-butyl group adjacent to the ether link. Suitable Lewis acids will be apparent to those skilled in the art and include for example aluminium trichloride or titanium tetrachloride in a suitable solvent, for example toluene.

Compounds of structure (XA) can be prepared for example by reacting a compound of structure (XI) with a and compound of structure (IVG)

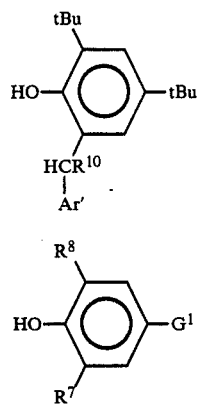 (XI)

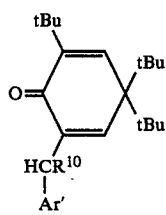 (IVG)

in which $G_1$, $R^7$, $R^8$, $R^{10}$ and Ar' are as described for compound (X). The reaction is carried out under conditions well known for the formation of diphenyl ethers, for example in an organic solvent in the presence of a suitable oxidant. Suitably the reaction is carried out in ether in the presence of manganese dioxide as an oxidant.

Alternatively, the compounds of structure (XA) can be prepared by reacting a compound of structure (XIA)

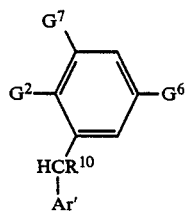 (XIA)

in which $R^{10}$ and Ar' are as described for structure (XI), with a compound of structure (IVG). The reaction can be carried out in an organic solvent, for example ether, in the presence of a suitable catalyst, for example copper, mercury or sodium metaperiodate.

Compound of structure (XIA) can be prepared by bromination of compounds of structure (XI) by standard methods.

The compounds of structure (IV), (IVA), (IVC), (IVD), (IVE) and (IVF) are known or can be prepared by known methods.

The compounds of structure (III), (V), (VA), (VI), (VII), (X), (XA), (XI) and (XIA) are novel and useful intermediates for the preparation of compounds of structure (I) and as such form a further aspect of the invention.

The intermediates of structure (III), (VA), (VI) and (XI) can together be represented by the structure:

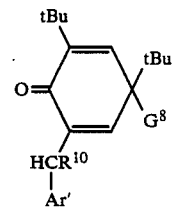

in which $G^6$ is t-butyl, halogen or XH; X is oxygen or sulphur; $G^7$ is hydrogen or t-butyl; $G^2$ is hydroxy, protected hydroxy or nitro; $R^{10}$ is hydrogen or $C_{1-4}$alkyl, and Ar' is 6-oxo-3(1H)-pyridyl, 6-oxo-3(1H)-pyridazinyl or a protected group Ar, with the proviso that when $G^6$ is t-butyl, then $G^7$ is t-butyl.

The intermediates of structure (XA) and (XIA) can together be represented by the structure

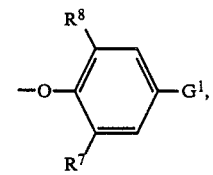

in which, $G^8$ is bromo or a group

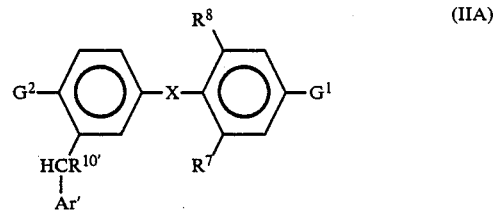

$G^1$ is a protected group $R^1$; $R^7$ and $R^8$ are hydrogen or halogen, $R^{10}$ is hydrogen or $C_{1-4}$alkyl and Ar' is a protected group Ar, 6oxo-3(1H)-pyridyl or 6-oxo-3(1H)-pyridazinyl.

Compounds of structure (I) wherein X is $CH_2$ may be prepared by methods analogous to those known in the art as described in the Jorgensen review monograph and references cited therein.

The products of reactions (a) to (h) are all compounds of structure (IIA)

(IIA)

in which
$G^1$ is $NO_2$, CHO, CN, $CH_2Hal$, a group $R^1$ or a protected group $R^1$; Hal is halogen;
$R^7$, $R^8$, and X are as described for structure (I);
$R^{10'}$ is hydrogen, $C_{1-4}$alkyl, —CHO, —$CO_2C_{1-4}$alkyl or cyano;
$G^2$ is $NO_2$, hydroxy or a protected hydroxy group;
Ar' is a protected group Ar, a 6-oxo-3(1H)-pyridyl group or a 6-oxo-3(1H)-pyridazinyl group; provided that, when $G^1$ is $NO_2$, $G^2$ is OH or a protected OH.

The compounds of structure (IIA) are novel and useful intermediates and form a further aspect of the invention.

The compounds of structure (IIA) can be converted to compounds of structure (I) by standard reactions well known in the art.

Compounds of structure (IIA) in which $G^1$ is $NO_2$, CN, $CH_2Hal$ or CHO, can be converted into compounds of structure (IIA) in which $G^1$ is a protected group $R^1$ by standard techniques as described by Harington C. R. (1948) Biochem. J. 43, 434; and Roche J., Michel, R. Nunez J. and Jacquemin C. (1956) C. R. Hebd Seances Acad. Sci. 244, 1507, and ibid 245, 77–80. For example, reduction of a compound of structure (IIA), in which $G^1$ is $NO_2$ with $SnCl_2$ in HCl followed by reaction with ammonium nitrite and copper I cyanide affords a compound of structure (IIA) wherein $G^1$ is CN. Further reaction with $SnCl_2$ in HCl affords a compound of structure (IIA) in which $G^1$ is CHO. Conversion of the aldehyde group so formed to a protected group $R^1$ may be accomplished by, for example, (i) where X is oxygen, treatment with N-acetylglycine to give an azlactone intermediate which undergoes hydrolysis and reduction to form a compound of structure (IIA) wherein $G^1$ is a protected group $R^1$ of structure

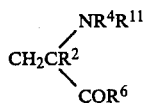

where $R^6$ is hydroxy, $R^4$ is hydrogen and $R^{11}$ is acetyl; alternatively, alcoholyis and reduction of the intermediate azlactone gives the desired compounds of structure (IIA) wherein $R^6$ is $C_{1-4}$alkoxy, or (ii) treatment with sodium borohydride followed by phosphorous tribormide, to form a group $CH_2Hal$ where Hal is brominde which may be reacted with an alkyl acetamido malonate, for example, ethyl acetamido malonate, to afford a compound of structure (IIA) wherein $G^1$ is a protected group $R^1$ of structure

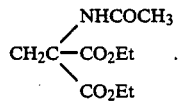

Deprotection using standard procedures affords the desired compounds of structure (I), wherein $R^4$ and $R^5$ are hydrogen and $R^6$ is Further chemical modifications to prepare protected groups $R^1$ are described in for example, "Amino Acids, Peptides and Proteins", Specialist periodical Reports, Royal Society of Chemistry, 1969, and succeeding years; "Comprehensive Organic Chemistry", E. Haslam, Ed., Pergamon Press, 1979, 5. 187; and "General and Synthetic Methods Specialist Periodical Reports", Royal Society of Chemistry, 1978, and succeeding years.

Compounds of structure (IIA) wherein $G^1$ is a protected group $R^1$ of structure $YCOR^6$ or $(CH_2)_2NR^4R^{11}$ may be prepared from compounds of structure (IIA) wherein $G^1$ is CHO by standard techniques.

Compounds of structure (IIA) in which $G^2$ is nitro can be converted into compounds of structure (IIA) in which $G^2$ is hydroxy by standard techniques. For example, by reduction of the nitro group to an amino group followed by diazotisation and hydrolysis to form the hydroxy group.

Compounds of structure (IIA) wherein $R^7$ and $R^8$ are both nitro, can be converted to other compounds of structure (IIA) wherein $R^7$ and $R^8$ are not both nitro, for example, (i) compounds of structure (IIA) wherein one of $R^7$ and $R^8$ is nitro and the other is amino, can be prepared by selective reduction of a compound of structure (IIA) wherein $R^7$ and $R^8$ are both nitro with, for example, iron in acetic acid and acetic anhydride, followed by deprotection of the intermediate acylamino group so formed at an appropriate time; alternatively, and preferably, transfer hydrogenation using cyclohexene and palladium affords directly a compound of formula (IIA) wherein one of $R^7$ and $R^8$ is nitro and the other is amino.

(ii) compounds of sturcture (IIA) wherein $R^7$ and $R^8$ are both amino can suitably be prepared by chemical reduction of a compound of structure (IIA) wherein $R^7$ and $R^8$ are both nitro with, for example, iron in acetic acid, or with $SnCl_2$; or, preferably, by catalytic reduction of such a compound of structure (IIA) with, for example, hydrogen in the presence of a suitable metal catalyst, for example, platinum or palladium on carbon;

(iii) compounds of structure (IIA) wherein $R^7$ and $R^8$ are both the same halogen atom can be prepared by diazotisation of a compound of structure (IIA) wherein $R^7$ and $R^8$ are both amino, with a suitable diazotising agent, for example sodium nitrite in sulphuric acid and acetic acid, followed by reaction of the intermediate bis-diazonium ion so formed with a suitable halogenating agent. For example, where, in structure (IIA) $R^7$ and $R^8$ are both bromine, treatment with copper I bromide and hydrogen bromide in the presence of urea. Other suitable halogenating agents depending on the nature of $R^7$ and $R^8$ in structure (IIA), for example treatment with potassium iodide and iodine affords a compound of formula (IIA) wherein $R^7$ and $R^8$ are both iodine.

(iv) compounds of structure (IIA) wherein $R^7$ and $R^8$ are different halogen atoms can be prepared from compounds of structure (IIA) wherein one of $R^7$ and $R^8$ is nitro and the other is amino. The amino group in the compound of structure (IIA) may be diazotised and then halogenated as hereinbefore described in (iii) to form a compound (IIA) wherein one of $R^7$ and $R^8$ is halogen and the other is nitro. Conversion of the nitro group, via reduction (to form a compound (IIA) wherein one of $R^7$ and $R^8$ is halogen and the other is amino), diazotisation and finally halogenation (using a different halogenating agent to that used in the first stage) affords a compound of structure (IIA) wherein $R^7$ and $R^8$ are different halogen atoms.

(v) compounds of structure (IIA) wherein one or both of $R^7$ and $R^8$ are hydrogen can be prepared by reduction of suitable diazonium or bis-diazonium salts prepared as described in (iii) and (iv).

Compounds of structure (I) wherein $R^4$ and $R^5$ are both hydrogen and/or $R^6$ is hydroxy may be converted to other compounds of structure (I). For example, (i) compounds of structure (I) wherein $R^4$ is hydrogen or $C_{1-4}$alkyl and $R^5$ is $C_{1-4}$alkanoyl may be prepared by acylation of a compound of structure (I) wherein $R^4$ is hdyrogen or $C_{1-4}$alkyl and $R^5$ is hydrogen.

(ii) compounds of structure (I) wherein $R^6$ is $C_{1-4}$alkoxy may be prepared by esterification of a compound of structure (I) wherein $R^6$ is hydroxy.

Compounds of structure (I) wherein $R^6$ is $-NR^4R^5$ can be prepared by reaction of a compound of structure (I) wherein $R^6$ is $C_{1-4}$alkoxy with ammonia or an appropriate amine.

The compounds of structure (I) exhibit biological activity which can be demonstrated in the following tests:

(i) the induction of mitochondrial α-glycerophosphate dehydrogenase (GPDH;EC 1.1.99.5). This assay is particularly useful since in certain species e.g. rats it is induced specifically by thyroid hormones and thyromimetics in a dose-related manner in responsive tissues e.g. liver, kidney and the heart (Westerfield, W. W, Richert, D. A. and Ruegamer, W. R., Endocrinology, 1965, 77, 802). The assay allows direct measurement in rats of a thyroid hormone-like effect of compounds and in particular allows measurement of the direct thyroid hormone-like effect on the heart;

(ii) the elevation of basal metabolic rate as measured by the increase in whole body oxygen consumption;

(iii) the stimulation of the rate of beating of atria isolated from animals previously dosed with thyromimetics;

(iv) the change in total plasma cholesterol levels as determined using a cholesterol oxidase kit (for example, the Merck CHOD iodide colourimetric kit)

(v) the measurement of LDL (low density lipoprotein) and HDL (high density lipoprotein) cholesterol in lipoprotein fractions separated by ultracentrifugation; and p (vi) the change in total plasma triglyceride levels as determined using enzymatic colour tests, for example the Merck System GPO-PAP method.

The compounds of structure (I) have been found to exhibit selective thyromimetic activity in these tests, (a) by increasing the metabolic rate of test animals, and raising hepatic GPDH levels at doses which do not significantly modify cardiac GPDH levels, and (b) by lowering plasma cholesterol and triglyceride levels, and the ratio of LDL to HDL cholesterol at doses which do not significantly modify cardiac GPDH levels.

The compounds of structure (I) may therefore be used in therapy, in the treatment of conditions which can be alleviated by compounds which selectively mimic the effects of thyroid hormones in certain tissues whilst having little or no direct thyromimetic effect on the heart. For example, compounds of structure (I) which raise hepatic GPDH levels and metabolic rate at doses which do not significantly modify cardiac GPDH levels are indicated in the treatment of obesity.

Compounds of structure (I) which lower total plasma cholesterol, the ratio of LDL-cholesterol to HDL-cholesterol and triglyceride levels at doses which do not significantly modify cardiac GPDH levels are indicated for use as general antihyperlipidaemic (antihyperlipoproteinaemic) agents i.e. in the treatment of patients having elevated plasma lipid (cholesterol and triglyceride) levels. In addition, in view of this effect on plasma cholesterol and triglyceride, they are also indicated for use as specific anti-hypercholesterolaemic and antihypertriglyceridaemic agents.

Patients having elevated plasma lipid levels are considered at risk of developing coronary heart disease or other manifestations of atherosclerosis as a result of their high plasma cholesterol and/or triglyceride concentrations. Further, since LDL-cholesterol is believed to be the lipoprotein which induces atherosclerosis, and HDL-cholesterol believed to transport cholesterol from blood vessel walls to the liver and to prevent the build up of atherosclerotic plaque, anti-hyperlipidaemic agents which lower the ratio of LDL-cholesterol to HDL cholesterol are indicated as anti-atherosclerotic agents.

The present invention also provides a method of producing selective thyromimetic activity in certain tissues except the heart which comprises administering to an animal in need thereof an effective amount to produce said activity of a compound of structure (I) or a pharmaceutically acceptable salt thereof.

The present invention also relates to a method of lowering plasma lipid levels and a method of lowering the ratio of LDL-cholesterol to HDL-cholesterol levels by suitably administering a compound of this invention or a pharmaceutically acceptable salt thereof.

In addition, compounds of structure (I) may be indicated in thyroid hormone replacement therapy in patients with compromised cardiac function.

In therapeutic use the compounds of the present invention are usually administered in a standard pharmaceutical composition.

The present invention therefore provides in a further aspect pharmaceutical compositions comprising a compound of structure (I) or a pharmaceutically acceptable salt thereof and a pharmaceutically acceptable carrier. Such compositions include those suitable for oral, parenteral or rectal administration.

Compounds of structure (I) and their pharmaceutically acceptable salts which are active when given orally can be formulated as liquids for example syrups, suspensions or emulsions, tablets, capsules and lozenges.

A liquid composition will generally consist of a suspension or solution of the compound or pharmaceutically acceptable salt in a suitable liquid carrier(s), for example ethanol, glycerine, sorbitol, non-aqueous solvent such as polyethylene glycol, oils or water, with a suspending agent, preservative, surfactant, wetting agent, flavouring or colouring agent. Alternatively, a liquid formulation can be prepared from a reconstitutable powder.

For example a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example polyvinylpyrrolidone. The tablet can also be provided with a colour film coating, or colour included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example liquid paraffin or fractionated coconut oil can be prepared and filled into a soft gelatin capsule.

Compound of structure (I) and their pharmaceutically acceptable salts which are active when given parenterally can be formulated for intramuscular or intravenous administration.

A typical composition for intra-muscular administration will consist of a suspension or solution of active ingredient in an oil, for example arachis oil or sesame oil. A typical composition for intravenous administration will consist of a sterile isotonic aqueous solution containing, for example active ingredient, dextrose, sodium chloride, a co-solvent, for example polyethylene glycol and, optionally, a chelating agent, for example ethylenediamine tetracetic acid and an anti-oxidant, for example, sodium metabisulphite. Alternatively, the solution can be freeze dried and then reconstituted with a suitable solvent just prior to administration.

Compounds of structure (I) and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

Compounds of structure (I) and their pharmaceutically acceptable salts which are active on topical administration can be formulated as transdermal compositions. Such compositions include, for example, a backing, active compound reservoir, a control membrane, liner and contact adhesive.

The typical daily dose of a compound of structure (I) varies according to individual needs, the condition to be treated and with the route of administration. Suitable doses are in the general range of from 0.001 to 10 mg/kg bodyweight of the recipient per day.

Within this general dosage range, doses can be chosen at which the compounds of structure (I) lower plasma cholesterol levels and raise metabolic rate with little or no direct effect on the heart. In general, but not exclusively, such doses will be in the range of from 0.5 to 10 mg/kg.

In addition, within the general dose range, doses can be chosen at which the compounds of structure (I) lower plasma cholesterol levels and have little or no effect on the heart without raising metabolic rate. In general, but not exclusively, such doses will be in the range of from 0.001 to 0.5 mg/kg.

It is to be understood that the 2 sub ranges noted above are not mutually exclusive and that the particular activity encountered at a particular dose will depend on the nature of the compound of structure (I) used.

Preferably, the compound of structure (I) is in unit dosage form, for example, a tablet or a capsule so that the patient may self-administer a single dose. In general, unit doses contain in the range of from 0.05–100 mg of a compound of structure (I). Preferred unit doses contain from 0.05 to 10 mg of a compound of structure (I).

The active ingredient may be administered from 1 to 6 times a day. Thus daily doses are in general in the range of from 0.05 to 600 mg per day. Preferably, daily doses are in the range of from 0.05 to 100 mg per day. Most preferably from 0.05 to 5 mg per day.

The following Examples illustrate the invention. Temperatures are recorded in degrees Centigrade.

EXAMPLE 1

L-3,5-Dibromo-3'-(6-oxo-3(1H)-pyridylmethyl)-thyronine (a) 5-Bromo-2-methoxypyridine (41.36 g) (prepared by the method of I. Kompis et al, European Journal of Medicinal Chemistry 1977, 12, 531) in dry tetrahydrofuran (50 ml) was cooled to −85° with stirring under a nitrogen atmosphere. n-Butyl lithium (137 ml of a 1.6M hexane solution) in dry tetrahydrofuran (50 ml) was added dropwise, keeping the temperature below −80°. After stirring for 5 minutes, 2-methoxybenzaldehyde (25.0 g) in dry tetrahydrofuran (150 ml) was added dropwise with stirring, keeping the temperature below −70°. The mixture was stirred whilst allowing to warm to room temperature, then quenched with saturated ammonium chloride solution (150 ml). The organic layer was separated and the aqueous was further extracted with ethyl acetate. The organic layers were combined, dried with anhydrous magnesium sulphate and evaporated to dryness to give an orange gum which was crystallised from dichloromethane/petroleum spirit (60°–80°) to give 1-(2-methoxyphenyl)-1-(6-methoxy-3-pyridyl)-methanol as a pale yellow solid (28.39 g, 63%) m.p. 83°–84°.

This reaction was also carried out using dry diethyl ether as solvent, keeping the temperature of the reaction mixture below −30° during the addition of the reagents.

(b) To a solution of this carbinol (28.30 g) in dry pyridine (120 ml) was added acetic anhydride (33 ml) and the solution gently warmed on a steam bath for 2 hours. The solvents were evaporated and to the residue was added an equivalent volume of 94% ethanol. On cooling the product crystallised to give 1-(2-methoxyphenyl)-1-(6-methoxy-3-pyridyl)-methyl acetate as a pale yellow crystalline solid (92%), m.p. 75°–77°.

(c) This acetylated carbinol (22.00 g) was hydrogenated in methanol (180 ml) over 10% palladium on charcoal (2.0 g) on a Parr apparatus at ambient temperature. After filtration and evaporation to dryness the resulting oil was filtered through a silica gel column by elution with ethyl acetate/petroleum spirit (60°–80°), gradient elution, to give 2-(6-methoxy-3-pyridylmethyl)anisole as a colourless oil (15.89 g, 91%).

(d) This anisole (72.9 g) was added slowly to a cooled mixture of trifluoroacetic acid (100 ml) and trifluoroacetic anhydride (100 ml). The resulting solution was added dropwise to a solution of iodine tris-trifluoroacetate (74.1 g, prepared by the method of Schmeisser et al., Ber., 1967, 100, 1633) in trifluoroacetic anhydride (120 ml) at −12° to −8°. The reaction mixture was kept at room temperature overnight, then the solvents were removed in vacuo keeping the internal temperature below 25°. The residue was dissolved in dichloromethane (500 ml) and poured into a well stirred solution (800 ml) containing sodium perchlorate (100 g) and sodium acetate (200 g). The crystalline product which deposited was collected (24.0 g), and recrystallised from ether-tetrahydrofuran to give 4,4'-dimethoxy-3,3'-bis(6-methoxy-3-pyridylmethyl)-diphenyl iodonium perchlorate, m.p. 168°–9°.

(e) The iodonium trifluoroacetate was prepared as follows. Iodine (83.1 g) was suspended in trifluoroacetic anhydride (300 ml) and stirred under nitrogen at 40° whilst fuming nitric acid (92.4 ml) was added over 45 minutes, keeping the temperature below 45° by external cooling. The mixture was maintained at 40° under a stream of nitrogen until all nitrogen oxides were removed, then the solvent was removed in vacuo. The residue was suspended in trifluoroacetic anhydride (300 ml) and 2-(6-methoxy-3-pyridylmethyl)-anisole (300 g) in trifluoroacetic anhydride (300 ml) and trifluoroacetic acid (300 ml) added with stirring, keeping the temperature below −15°. The reaction mixture was stirred at room temperature for 24 hours, evaporated to dryness, dissolved in dichloromethane (200 ml), and poured into a stirred mixture of petroleum spirit (2 liters) and sodium acetate (1 kg) in water (5 liters). The pH was adjusted to 6 with additional sodium acetate and the mixture stirred overnight. The mother liquors were decanted from the gum-like product which was taken up in dichloromethane (500 ml) and poured into vigourously stirred ether (6 liters). After 0.5 hour the mixture was filtered to give 4,4'-dimethoxy-3,3'-bis-(6-methoxy-3-pyridylmethyl)-diphenyl iodonium trifluoro-acetate (350 g, 77%), m.p. 132°–4°.

(f) L-3,5-Dibromotyrosine (500 g) was suspended in methanol (5 liters) and dry hydrogen chloride passed through the stirred suspension for 5 hours. The reaction mixture was evaporated to dryness, the residue suspended in water (4 liters), and the pH adjusted to 6 with 40% sodium hydroxide. The precipitate was collected and washed with water to give L-3,5-dibromotyrosine methyl ester (467 g, 90%), m.p. 201°–203°. The ester (768 g) was suspended in chloroform (2.7 liters) and ethyl acetate (2.7 liters), then trifluoroacetic anhydride (565 g) was added over 0.5 hour, keeping the temperature below 35°. The mixture was left overnight, then water (2 liters) was added and the pH adjusted to 7 by the addition of saturated sodium bicarbonate solution. The organic layer was removed, washed with water, dried with anhydrous magnesium sulphate and evaporated. The residue was recrystallised from aqueous methanol to give L-3,5-dibromo-N-trifluoroacetyl-tyrosine methyl ester (786 g, 81%), m.p. 136–7°.

(g) To a stirred solution of the iodonium perchlorate (91.3 g), L-3,5-dibromo-N-trifluoroacetyltyrosine methyl ester (72.0 g) and triethylamine (25 ml) in dry dichloromethane (2 liters) was added copper bronze (10.0 g). The mixture was stirred at room temperature for 19 hours, filtered, and the filtrate washed successively with aqueous acetic acid, 0.2N sodium hydroxide, then saturated sodium chloride solution. The solution was dried over anhydrous magnesium sulphate, evaporated to dryness and chromatographed on silica gel. Elution with dichloromethane gave initially 4-iodo-2-(6-methoxy-3-pyridylmethyl)-anisole (37 g, 78%), m.p. 68°–70°, followed by 3,5-dibromo-3'-(6-methoxy-3(1H)-pyridylmethyl)-O-methyl-N-trifluoroacetyl-thyronine methyl ester (39.45 g, 44%) m.p. 125°–126° (from dichloromethane/petroleum spirit).

(h) This dibromothyronine (25.77 g) was dissolved in dry dichloromethane (225 ml) and cooled with stirring to −55°. A solution of boron tribromide (23.0 ml) in dry dichloromethane (50 ml) was added dropwise, then the mixture was allowed to warm to room temperature. After 2 hours, the purple reaction mixture was poured into an ice-cold solution of sodium acetate (100 g) in water (400 ml). The mixture was thoroughly extracted with ethyl acetate, the organic extracts evaporated, then the residue dissolved in glacial acetic acid (1 liter) and concentrated hydrochloric acid (500 ml). The solution was refluxed for 16.5 hours, then evaporated to dryness. The residue was recrystallised from aqueous ethanolic sodium hydroxide on addition of glacial acetic acid to pH5 to give L-3,5-dibromo-3'-(6-oxo-3(1H)-pyridylmethyl)thyronine (19.0 g, 93%), m.p. 269°–71° (dec.).

Alternatively, the title compound was prepared as follows.

(i) To a stirred suspension of 5-hydroxy-2-methoxybenzaldehyde (306.6 g, prepared by the method of Ulrich et al, *J. Org. Chem.*, 1974, 39, 2437), benzyl bromide (355.8 g) and Adogen 464 (48.5 g) in dichloromethane (600 ml) was added a solution of sodium hydroxide (123.5 g) in water (500 ml). The mixture became warm and the suspension dissolved; additional dichloromethane (300 ml) was added to prevent crystallisation of the benzylated product. After 2 hours, the organic layer was removed, washed twice with water, once with saturated sodium chloride solution, then dried with anhydrous magnesium sulphate. The solution was concentrated, then treated with petroleum spirit to give 5-benzyloxy-2-methoxybenzaldehyde (445.7 g, 91%), m.p. 99°–100°.

(j) 5-Bromo-2-methoxypyridine (15.87 g) was dissolved in dry tetrahydrofuran (50 ml) and the solution cooled with mechanical stirring under nitrogen to −100° (ether/liquid nitrogen). A solution of n-butyl lithium in hexane (53 ml of a 1.6M solution) was added dropwise, maintaining the temperature below −90°; a white precipitate appeared. After 5 minutes, 5-benzyloxy-2-methoxybenzaldehyde (17.04 g) in dry tetrahydrofuran (150 ml) was added dropwise, maintaining the temperature below −95°. After the addition was complete, the mixture was stirred to 5°. The dark solution was quenched with excess saturated ammonium chloride, the organic layer removed, the aqueous extracted with ethyl acetate, then the combined organics dried with anhydrous magnesium sulphate and evaporated. The residue crystallised from ether/petroleum spirit to give 1-(5-benzyloxy-2-methoxyphenyl)-1-(6-methoxy-3-pyridyl)methanol (17.83 g, 72%), m.p. 80°–82°.

(k) To a solution of the carbinol (17.83 g) in dry pyridine (60 ml) was added acetic anhydride (70 ml). The solution was heated to 90° and after 5 minutes evaporated to dryness. The residue crystallised from ether/petroleum spirit to give 1-(5-benzyloxy-2-methoxyphenyl)-1-(6-methoxy-3-pyridyl)-methyl acetate (19.08 g, 96%), m.p. 94°.

(l) A suspension of the acetate (19.0 g) in methanol (150 ml) containing 10% palladium on charcoal (3.0 g) was hydrogenated in a Parr apparatus. When two moles of hydrogen had been consumed, the mixture was filtered and evaporated to dryness. The residue was crystallised from chloroform/petroleum spirit to give 4-methoxy-3-(6-methoxy-3-pyridylmethyl)-phenol (10.91 g, 92%), m.p. 121°–4°.

(m) L-3,5-Dinitrotyrosine (960 g) was suspended in dry ethanol (7.51) and dry hydrogen chloride passed through the refluxing solution. The solution was cooled, the solid precipitate collected, and the filtrate concentrated to give a second crop. The combined crops were suspended by stirring in water (101) and sodium acetate was added to pH3. The precipitate was collected, washed and dried to give L-3,5-dinitrotyrosine ethyl ester (760 g), which was suspended in chloroform (2.51) and ethyl acetate (2.51). To the stirred suspension was added trifluoroacetic anhydride (1 kg) in ethyl acetate (500 ml), over 1 hour. The solution was concentrated, the resulting precipitate collected and washed with petroleum spirit (40°–60°) to give L-3,5-dinitro-N-trifluoroacetyltyrosine ethyl ester (788 g, 78%), m.p. 115°–6°.

(n) To a dark orange suspension of L-3,5-dinitro-N-trifluoroacetyl tyrosine ethyl ester (132.58 g) in dry pyridine (300 ml) was added methanesulphonyl chloride (38.38 g) with rapid stirring. The dark solution was stirred and refluxed for 10 minutes, then 4-methoxy-3-(6-methoxy-3-pyridylmethyl)-phenol (75.00 g) in dry pyridine (300 ml) was added and the resulting mixture stirred and refluxed for 1 hour. The pyridine was evaporated and the residue dissolved in chloroform, washed with water, 2N hydrochloric acid, water, saturated sodium bicarbonate (twice), 2N sodium hydroxide (twice), water (twice) then dried with anhydrous magnesium sulphate. The solution was concentrated to approximately 250 ml and combined with the mother liquors of a second batch (carried out on the same scale). To this combined chloroform solution was added activated charcoal and the mixture warmed on a steam bath for approximately 10 minutes, cooled, filtered and evaporated to dryness to give a dark orange gum (246.40 g) which was crystallised from aqueous ethanol to give L-3,5-dinitro-3'-(6-methoxy-3-pyridylmethyl)-O-methyl-N-trifluoroacetyl thyronine ethyl ester as a dusky orange solid (176.10 g, 48%), m.p. 123°–4°.

(o) This dinitrothyronine was hydrogenated in glacial acetic acid (30 ml) over 10% palladium on charcoal (1.50 g) using a Parr hydrogenator. The mixture was filtered and the solution added to a well stirred solution of sodium nitrite (2.14 g) in concentrated sulphuric acid (90 ml) and glacial acetic acid (40 ml) under nitrogen keeping the temperature below −10°. This reaction mixture was poured onto a vigorously stirred solution of cuprous bromide (4.48 g) and urea (2 g) in 48% aqueous hydrobromic acid (120 ml) and chloroform (120 ml). After 2 hours water (approximately 80 ml) was added, the organic layer separated, and the aqueous was further extracted with chloroform. The combined chloroform extracts were washed with water (4 times), saturated sodium bicarbonate solution (3 times), water, saturated sodium chloride solution, then dried with anhydrous magnesium sulphate and evaporated to give an orange gum (5.71 g). Purification by column chromatography on silica gel, eluting with ethyl acetate/petroleum spirit (60°–80°) [1:5], afforded L-3,5-dibromo-3'-(6-methoxy-3-pyridylmethyl)-O-methyl-N-trifluoroacetyl thyronine ethyl ester, which was recrystallised from ethyl acetate/petroleum spirit (60°–80°) (3.12 g, 44%), m.p. 129°–130°. This compound was also prepared by forming the bis-diazonium salt under aqueous conditions.

(p) This dibromo compound (3.02 g) was dissolved in glacial acetic acid (150 ml) and 48% aqueous hydrobromic acid (80 ml) and the solution refluxed for 5 hours. The solvents were removed in vacuo and the residue recrystallised twice from aqueous ethanolic sodium hydroxide on addition of acetic acid to pH6 to give L-3,5-dibromo-3'-(6-oxo-3(1H)-pyridylmethyl)-thyronine (1.41 g, 60%), identical in all respects with the sample obtained in (h) above.

EXAMPLE 2

L-3,5-Diiodo-3'-(6-oxo-3(1H)-pyridylmethyl)-thyronine (a) L-3,5-Diiodotyrosine was successively esterified and trifluoroacetylated as described in Example 1(f) to give L-3,5-diiodo-N-trifluoroacetyl thyronine methyl ester, m.p. 175°–7°.

(b) This ester (11.3 g) was treated with the iodonium perchlorate described in Example 1(d) (11.3 g) in the presence of copper bronze (2.0 g) and triethylamine (6.0 g) in dichloromethane (200 ml) according to the method of Example 1(g) to give L-3,5-diiodo-3'-(6-methoxy-3-pyridylmethyl)-O-methyl-N-trifluoroacetyl)-thyronine methyl ester (6.3 g, 56%), m.p. 123°–4°.

(c) This diiodothyronine (5.75 g) was treated successively with boron tribromide then hydrochloric and acetic acids as described in Example 1(h), to give L-3,5-diiodo-3'-(6-oxo-3(1H)-pyridylmethyl)-thyronine (4.5 g, 95%), m.p. 253°–5° (dec).

Alternatively, the title compound was prepared as follows:

(d) L-3,5-Dinitro-3'-(6-methoxy-3-pyridylmethyl)-O-methyl-N-trifluoroacetyl thyronine ethyl ester (6.23 g, prepared as described in Example 1(n)) was hydrogenated in glacial acetic acid (30 ml) in the presence of 10% palladium on charcoal (1.5 g). When uptake of hydrogen had ceased, the mixture was filtered and added to a cold (0°) solution of sulphuric acid (3.94 g) in water (50 ml). The soluion was stirred at −10° to −15° while a solution of sodium nitrite (1.73 g) in water (50 ml) was added dropwise. The resulting black semisolid mixture was added to a stirred mixture of potassium iodide (20 g), iodine (4 g) and urea (1 g) in water (200 ml) and chloroform (200 ml). The mixture was stirred for 1 hour, then treated with excess sodium metabisulphite. The organic layer was removed and washed successively with water, saturated sodium bicarbonate, water, then saturated sodium chloride. The solution was dried with anhydrous sodium sulphate, evaporated to dryness, and the residue chromatographed on silica gel (200 g). Elution with ethyl acetate/petroleum spirit (60°–80°) (1:6), then recrystallisation from ethyl acetate/petroleum spirit (60°–80°) gave L-3,5-diiodo-3'-(6-methoxy-3-pyridylmethyl)-O-methyl-N-trifluoroacetyl thyronine ethyl ester (2.72 g, 35%), m.p. 105°–9°. The diazotisation can be carried out using excess sulphuric acid as a co-solvent under aqueous conditions or under anhydrous conditions as in Example 1(o).

(e) This diiodo compound (2.64 g) was treated with 48% aqueous hydrogen bromide (135 ml) and glacial acetic acid (270 ml) as described in Example 1(p) to give L-3,5-diiodo-3'-(6-oxo-3(1H)-pyridylmethyl)-thyronine (1.76 g, 82%), identical in all respects to the product obtained in (c) above.

EXAMPLE 3

L-3,5-Dichloro-3'-(6-oxo-3(1H)-pyridylmethyl)-thyronine (a) L-3,5-Dichlorotyrosine was successively esterified and trifluoroacetylated as described in Example 1(f) to give L-3,5-dichloro-N-trifluoroacetyl tyrosine methyl ester, m.p. 123°–4°.

(b) This ester (7.6 g) was treated with the iodonium perchlorate (Example 1(d), 13.7 g) in the presence of copper bronze (3.0 g) and triethylamine (3 g) in dichloromethane (200 ml) according to the method of Example 1(g) to give L-3,5-dichloro-3'-(6-methoxy-3-pyridylmethyl)-O-methyl-N-trifluoroacetyl thyronine methyl ester (7.3 g, 62%), m.p. 127°–8°.

(c) This dichlorothyronine (5.87 g) was treated successively with boron tribromide then hydrochloric and acetic acids as described in Example 1(h) to give L-3,5-dichloro-3'-(6-oxo-3(1H)-pyridylmethyl)-thyronine (4.22 g, 94%), m.p. 235° (dec).

Alternatively, the title compound was prepared as follows:

(d) L-3,5-Dinitro-3'-(6-methoxy-3-pyridylmethyl)-O-methyl-N-trifluoroacetyl thyronine ethyl ester (4.60 g, prepared as in Example 1(n)) was hydrogenated in glacial acetic acid (30 ml) over 10% palladium on charcoal (1.0 g) using a Parr hydrogenator. The mixture was filtered and the bis-diazonium salt prepared as described in Example 1(o). This reaction mixture was poured onto a vigorously stirred solution of cuprous chloride (2.28 g) and urea (1.6 g) in concentrated hydrochloric acid (85 ml) and chloroform (85 ml). After 2 hours this reaction mixture was worked up as in Example 1(o). Purification by column chromatography on silica gel, eluting with ethyl acetate/petroleum spirit (60°–80°) [1:5], afforded L-3,5-dichloro3'-(6-methoxy-3- pyridylmethyl)-

O-methyl-N-trifluoroacetyl thyronine ethyl ester, which was recrystallised from ethyl acetate/petroleum spirit (60°–80°) [1:8](0.42 g, 9%), m.p. 127°–132°.

(e) This dichloro compound (0.40 g) was deprotected using boron tribromide followed by concentrated hydrochloric acid in acetic acid, as described in Example 1(h), to give L-3,5-dichloro-3'-(6-oxo-3(1H)-pyridylmethyl)thyronine having analytical and spectral characteristics comparable with the product prepared in (c) above.

EXAMPLE 4

L-4-(4'-Hydroxy-3'-(6-oxo-3(1H)-pyridylmethyl)-phenylthio)3,5-diiodophenylalanine (a) To dry acetic acid (250 ml, dried by refluxing with 5% acetic anhydride for 4.5 hours) was added dry chlorine (16.00 g). Lead thiocyanate (36.48 g) was added in portions with rapid stirring then after 40 minutes 2-(6-methoxy-3-pyridylmethyl)-anisole (45.85 g) in dry acetic acid (175 ml) was added slowly from a dropping funnel. The mixture was stirred at room temperature for 20 hours, filtered, poured into water (approximately 2 liters) and extracted with chloroform. The combined chloroform extracts were washed with water, 2N sodium hydroxide, water, then dried with anhydrous magnesium sulphate and evaporated to dryness to give an orange gum which was crystallised from chloroform/petroleum spirit (60°–80°) to give 4-methoxy-3-(6-methoxy-3-pyridylmethyl)phenylthiocyanate as a yellow solid (39.89 g, 55%), m.p. 56°–58°.

(b) Sodium hydroxide (17.76 g) in water (120 ml) was added to a suspension of the thiocyanate (31.71 g) in 1,4-dioxan (120 ml) and the mixture was refluxed with stirring, under a nitrogen atmosphere, for 5 hours. The mixture was cooled and acidified to pH approximately 4 with concentrated hydrochloric acid, then chloroform (approximately 300 ml) and water (approximately 300 ml) were added. The organic layer was separated, washed with water, dried with anhydrous magnesium sulphate and evaporated to give a yellow gum (28.71 g), which was a mixture of the required thiol and the corresponding disulphide. The mixture was separated by column chromatography using silica gel by elution with ethyl acetate/petroleum spirit (60°–80°). 4-Methoxy-3-(6-methoxy-3-pyridylmethyl)-thiophenol was first isolated (2.55 g).

4,4'-Dimethoxy-3,3'-bis-(6-methoxy-3-pyridylmethyl)diphenyl-disulphide was later isolated (23.04 g), m.p. 59°–62°.

(c) The disulphide (19.44 g) was dissolved in 1,4-dioxan (100 ml) and water (25 ml) was added followed by triphenylphosphine (9.79 g) and concentrated hydrochloric acid (4 drops). The mixture was heated, with stirring, at 45° (oil bath temperature) for 0.5 hour. The solvents were evaporated and the residue dissolved in ethyl acetate, washed with water, dried with anhydrous magnesium sulphate and evaporated to dryness to give a colourless oil (27.40 g) which was chromatographed on silica gel. Elution with 5% ethyl acetate/petroleum spirit (60°–80°) gave 4-methoxy-3-(6-methoxy-3-pyridylmethyl)-thiophenol as a colourless oil (15.51 g) which had spectral and chromatographic characteristics comparable with the authentic product above.

(d) To L-3,5-dinitro-N-trifluoroacetyl tyrosine ethyl ester (14.33 g, Example 1(m)) in dry pyridine (40 ml) was added methanesulphonyl chloride (2.8 ml) with rapid stirring and the solution refluxed with stirring for 10 minutes. 4-Methoxy-3-(6-methoxy-3-pyridylmethyl)-thiophenol (8.67 g) in dry pyridine (40 ml) was added and the mixture refluxed, with stirring, for 20 minutes. Work-up of the reaction using the procedure of Example 1(n) gave L-3,5-dinitro-4-(4'-methoxy-3'-(6-methoxy-3-pyridylmethyl)-phenylthio)-N-trifluoroacetyl phenylalanine ethyl ester as a yellow solid (14.35 g, 68%), m.p. 115°–119° (from ethanol/water).

(e) Iodination of the dinitro compound (3.65 g) using the procedure of Example 2(d) gave L-3,5-diiodo-4-(4'-methoxy-3'-(6-methoxy-3-pyridylmethyl)-phenylthio)-N-trifluoracetyl phenylalanine ethyl ester as white powdery solid (1.18 g, 26%), m.p. 144°–145°.

(f) To a stirred solution of this diiodo compound (1.16 g) in dry dichloromethane (20 ml), cooled to −74°, was added boron tribromide (1.40 ml). The mixture was stirred whilst warming to room temperature and after 3 hours was poured onto ice/water. Ethyl acetate (50 ml) was added, the organic layer separated, washed with water (twice), then dried with anhydrous magnesium sulphate and evaporated to dryness to give the crude product as an off-white solid (1.0 g). This was combined with a further batch (0.62 g), and purified by medium pressure chromatography on silica gel using toluene/acetic acid [20:1, then 10:1] as eluant to give L-3,5-diiodo-4-(4'-hydroxy-3'-(6-methoxy-3-pyridylmethyl)-phenylthio)-N-trifluoroacetyl phenylalanine as an off-white solid (1.15 g, 66%), m.p. 157°–162°.

(g) This diiodo compound (0.95 g) was dissolved in glacial acetic acid (20 ml) and concentrated hydrochloric acid (20 ml) and the solution refluxed, with stirring, for 16 hours. The solvents were evaporated and the resulting solid was collected and dissolved in aqueous ethanolic sodium hydroxide, filtered, then acidified to pH6 with glacial acetic acid. Addition of some water aided precipitation of a solid which was collected and washed with water, then ethanol and finally with ether. This product was combined with another smaller batch (0.13 g) and further recrystallised in the manner described above to afford L-4-(4'-hydroxy-3'-(6-oxo-3(1H)-pyridylmethyl)phenylthio)-3,5-diiodophenylalanine as a cream coloured solid (0.78 g, 79%), m.p. 270°–273° (dec.).

EXAMPLE 5

L-3,5-Dibromo-4-(4'-hydroxy-3'-(6-oxo-3(1H)-pyridylmethyl)-phenylthio)-phenylalanine (a) Bromination of L-3,5-dinitro-4-(4'-methoxy-3'-(6-methoxy-3-pyridylmethyl)-phenylthio-N-trifluoroacetyl phenylalanine ethyl ester (4.00 g, prepared as in Example 4(d)) using the procedure of Example 1(o) gave L-3,5-dibromo-4-(4'-methoxy-3'-(6-methoxy-3-pyridylmethyl)phenylthio)-N-tifluoroacetyl phenylalanine ethyl ester as a cream coloured solid (0.75 g, 17%), m.p. 111°–113°. This compound was also prepared by forming the bis-diazonium salt in an aqueous medium as in Example 4(e).

(b) This dibromo compound (1.12 g) was deprotected using boron tribromide followed by concentrated hydrochloric acid in acetic acid as described in Example 1, to give L-3,5-dibromo-4-(4'-hydroxy-3'-(6-oxo-3(1H)-pyridylmethyl)-phenylthio)-phenylalanine as an off-white solid (0.71 g, 81%), m.p. 287°–289°.

EXAMPLE 6

L-3,5-Dinitro-3'-(6-oxo-3(1H)-pyridylmethyl)-thyronine hydrobromide

L-3,5-Dinitro-3'-(6-methoxy-3-pyridylmethyl)-O-methyl-N-trifluoroacetyl thyronine ethyl ester (2.50 g, as prepared in Example 1(n)) was stirred and refluxed in glacial acetic acid (15 ml) and 48% aqueous hydrogen bromide (15 ml) for 4 hours. The solvents were evaporated and the resulting red gum triturated with water and cooled. The crude product was collected by filtration and recrystallised five times from water/acetic acid/concentrated hydrogen bromide (6:2:1) to give L-3,5-dinitro-3'-(6-oxo-3(1H)-pyridylmethyl)-thyronine hydrobromide as a pale yellow solid (1.04 g), m.p. 195° (dec).

EXAMPLE 7

L-3-Amino-5-nitro-3'-(6-oxo-3(1H)-pyridylmethyl)-thyronine (a) L-3,5-Dinitro-3'-(6-methoxy-3-pyridylmethyl)-O-methyl-N-trifluoroacetyl thyronine ethyl ester (8.50 g, as prepared in Example 1(n)) was stirred in glacial acetic acid (80 ml) containing acetic anhydride (3.23 ml) and iron powder (7.50 g) at 100° (oil bath) for 1.5 hours. The mixture was cooled, filtered and evaporated to dryness to give a brown gum which was dissolved in chloroform, washed with water (3 times), saturated sodium chloride solution then dried with anhydrous magnesium sulphate and evaporated to give an orange gum (10.11 g). This was purified by column chromatography on silica gel with gradient elution using toluene/acetic acid to give a mustard coloured solid (2.65 g) which was crystallised from ethyl acetate/petroleum spirit (60°-80°) [1:4] to afford L-3-acetamido-3'-(6-methoxy-3-pyridylmethyl)-O-methyl-5-nitro-N-trifluoroacetyl thyronine ethyl ester as a white solid (2.33 g, 27%), m.p. 142°-144°.

(b) This acetamido compound (2.22 g) was dissolved in 48% aqueous hydrogen bromide (10 ml) and glacial acetic acid (20 ml) and the solution refluxed for 7.5 hours. The solvents were evaporated, the residual gum dissolved in aqueous ethanol, the solution filtered and cooled, then 0.88 ammonia added to pH approximately 8. Glacial acetic acid was added dropwise to pH approximately 6, the resulting yellow solid collected and recrystallised from aqueous ethanolic ammonia (pH approximately 8) on addition of glacial acetic acid to pH approximately 6 to give L-3-amino-5-nitro-3'-(6-oxo-3(1H)-pyridylmethyl)-thyronine as a yellow solid (0.85 g, 55%), m.p. 230°-235°.

EXAMPLE 8

DL-3,5-Dimethyl-3'-(6-oxo-3(1H)-pyridylmethyl)-thyronine (a) 2-Methoxy-5-(2-methoxy-5-(2,6-dimethyl-4-formylphenoxy)benzyl)-pyridine was synthesised by two methods:

(i) To a stirred solution of 4-iodo-2-(6-methoxy-3-pyridylmethyl)-anisole (7.20 g, obtained as described in Example 1(g)) and 2,6-dimethyl-4-formyl phenol (3.35 g) in dry pyridine (25 ml) was added anhydrous potassium carbonate (1.56 g) and the mixture heated to 150° (oil bath temperature) under a nitrogen atmosphere. Cupric oxide (2 g) was added and the black mixture stirred at 150±2° for 6 hours. The mixture was cooled and combined with a second reaction mixture (having used 4.00 g of the iodo compound and 1.73 g of the phenol). This mixture was poured into water and extracted with chloroform. The combined chloroform extracts were washed successively with water, 2N hydrochloric acid (twice), water, 2N sodium hydroxide (twice), then dried with anhydrous magnesium sulphate and evaporated to dryness to give a dark brown gum (7.47 g) which was purified by column chromatography on silica gel. Elution with ethyl acetate/petroleum spirit 60°-80° [1:10] gave the required product (2.32 g, 19%), m.p. 104°-105° (from ether/petroleum spirit (60°-80°) [1:5]).

(ii) A mixture of 4,4'-dimethoxy-3,3'-bis-(6-methoxy-3-pyridylmethyl)-diphenyl iodonium perchlorate (2.80 g, prepared as in Example 1(d)), 2,6-dimethyl-4-formylphenol (0.61 g), potassium t-butoxide (0.45 g), dicyclohexano-18-crown-6 (approximately 10 mg) and activated copper bronze (50 mg) were stirred in dry dichloromethane (10 ml) for 4 hours. Chloroform was added to the mixture, which was then filtered and evaporated to give an orange/brown gum (2.69 g), which was combined with the product from a further reaction (having used 0.10 g of the iodonium salt and 0.021 g of the phenol). This crude mixture was dissolved in chloroform, washed with water, 2N sodium hydroxide (twice), water, then dried with anhydrous magnesium sulphate and evaporated to dryness to give an orange gum (2.25 g). Purification by column chromatography on silica gel by elution with ethyl acetate/petroleum spirit (60°-80°) [1:10] gave a pale yellow solid, m.p. 103°-104° (from ether/petroleum spirit (60°-80°) [1:5]). Analytical and spectral data were comparable to those of the product synthesised by method (i) above.

(b) 2-Methoxy-5-(2-methoxy-5-(2,6-dimethyl-4-formylphenoxy)benzyl)-pyridine (10.84 g), N-acetylglycine (5.38 g), sodium acetate (3.77 g) and acetic anhydride (70 ml) were stirred at 100±5°, (oil bath temperature) for 24 hours. The solution was cooled and evaporated to leave a brown gum which was triturated with water, then with methanol to afford 2-methyl-4-(3,5-dimethyl-4-(4-methoxy-3-(6-methoxy-3-pyridylmethyl)-phenoxy)-benzal)-5-oxazolone as a yellow solid (8.27 g, 64%), m.p. 164°-165°.

(c) A solution of the azlactone (8.20 g) in 2N sodium hydroxide (50 ml) and ethanol (50 ml) was stirred at 65° (oil bath temperature) for 0.5 hours. The solvents were evaporated and the residual gum crystallised from aqueous ethanol to give a brown solid (8.02 g). Recrystallisation from aqueous acetic acid gave α-acetamido-β-[3,5-dimethyl-4-(4-methoxy-3-(6-methoxy-3-pyridylmethyl)-phenoxy)-phenyl]-1-propenoic acid as a beige coloured solid (6.84 g, 80%), m.p. 200°-202°.

(d) This acid (5.92 g) was hydrogenated in glacial acetic acid (80 ml) over 10% palladium on charcoal (0.5 g) at 45° in a Parr apparatus for 8 hours. The mixture was filtered, evaporated to dryness and the resulting brown solid purified by column chromatography on silica gel, eluting with toluene-acetic acid [5:1]. The starting acid was first isolated as light brown solid (3.23 g) followed by the required product as an off-white solid (2.23 g). Further purification by chromatography gave DL-N-acetyl-3,5-dimethyl-O-methyl-3'-(6-methoxy-3-pyridylmethyl)thyronine as an off-white solid (0.94 g), m.p. 186°-188°.

(e) This acid (0.88 g) was dissolved in 48% aqueous hydrogen bromide (8 ml) and glacial acetic acid (16 ml) and the solution refluxed with stirring for 5 hours. The solvents were evaporated to leave a brown solid which was combined with three other smaller batches and recrystallised twice from aqueous ethanolic sodium hydroxide by addition of acetic acid to pH approximately 6 to give DL-3,5-dimethyl-3'-(6-oxo-3(1H)-pyridylmethyl)thyronine as a cream coloured solid (1.11 g), m.p 250°–253°.

EXAMPLE 9

L-3,5-Diiodo-3'-[1-(6-oxo-3(1H)-pyridyl)-ethyl]-thyronine (a) 2,5-Dimethyoxyacetophenone (341 g) was added to cooled stirred sulphuric acid (21) under nitrogen. The solution was heated with stirring at 50±5° for 72 hours, cooled, and poured onto crushed ice (7.5 kg). The mixture was extracted with ether (twice with 1 liter then once with 0.5 liter), then the combined organics extracted with 2N sodium hydroxide (three times with 1 liter). The combined alkaline extracts were acidified with concentrated hydrochloric acid and the resulting precipitate collected, washed with water and dried to give 5-hydroxy-2-methoxyacetophenone (132.4 g, 42%), m.p. 82°–83°.

(b) This phenol (66.52 g) was dissolved in dichloromethane (800 ml) containing benzyl bromide (82.1 g) and Adogen 464 (18.6 g). A solution of sodium hydroxide (48.0 g) in water (800 ml) was added and the mixture stirred at room temperature for 2.5 hours. The organic layer was removed, washed with water (three times), then dried with anhydrous sodium sulphate and evaporated. The residue crystallised from petroleum spirit to give 5-benzyloxy-2-methoxyacetophenone (94.33 g, 92%), m.p, 49°–50°.

(c) To a stirred solution of 5-bromo-2-methoxypyridine (42.31 g) in dry tetrahydrofuran (180 ml) under nitrogen at −100° (liquid nitrogen/ether) was added a solution of n-butyl lithium in hexane (141 ml of a 1.6M solution) in dry tetrahydrofuran (110 ml), maintaining the temperature below −95°. A solution of 5-benzyloxy-2-methoxyacetophenone (38.44 g) in dry tetrahydrofuran (120 ml) was added, again maintaining the temperature below −95°. After the addition was complete, the reaction temperature was allowed to rise to −7°, then excess saturated ammonium chloride solution was added. The organic layer was removed and the aqueous extracted with ethyl acetate. The combined organics were dried with sodium sulphate and evaporated to give an oil which crystallised from dichloromethane/petroleum spirit (60°–80°) to give 1-(5-benzyloxy-2-methoxyphenyl)-1-(6-methoxy-3-pyridyl)-ethanol (36.12 g, 66%), m.p. 53°–4°.

(d) This carbinol (35.98 g) was dissolved in methanol (145 ml), 10% palladium on charcoal (5.9 g) added, and the mixture hydrogenated in a Parr apparatus. When uptake of hydrogen was complete, concentrated hydrochloric acid (1 ml) was added, the mixture filtered and the filtrate evaporated to dryness. The residue was taken up in acetic acid (150 ml), fresh 10% palladium on charcoal (6.0 g) added, and the mixture hydrogenated in a Parr apparatus at 60° under three atmospheres of hydrogen, until hydrogen uptake ceased (5 hours). The cooled mixture was filtered, then evaporated to dryness and the residue dissolved on chloroform. The chloroform solution was washed with saturated sodium bicarbonate solution, then dried with anhydrous sodium sulphate and evaporated to dryness. The residue was subjected to column chromatography on silica gel (300 g). Elution with chloroform gave 4-methoxy-3-[1-(6-methoxy-3-pyridylethyl] -phenol (6.1 g, 24%) as a waxy glass which did not crystallise.

(Found: C, 69.54; H, 6.93; N, 5.51; $C_{15}H_{17}NO_3$ Requires: C, 69.48; H, 6.61; N, 5.40%).

(e) Reaction of this phenol (6.0 g) with L-3,5-dinitro-N-trifluoroacetyl tyrosine ethyl ester was carried out as described in Example 1(n) to give, after column chromatography on silica gel, L-3,5-dinitro-3'-[1-(6-methoxy-3-pyridyl)-ethyl]-O-methyl-N-trifluoroacetyl thyronine ethyl ester (5.2 g, 35%) as a yellow froth which did not crystallise.

(Found: C, 52.00; H, 4.24; N, 8.49. $C_{28}H_{27}F_3N_4O_{10}$. Requires: C, 52.83; H, 4.28; N, 8.80%).

(f) This dinitro compound (5.1 g) was hydrogenated, bis-diazotised and iodinated as described in Example 2(d) to give L-3,5-diiodo-3'-[1-(6-methoxy-3-pyridyl)-ethyl]-O-methyl-N-trifluoroacetyl thyronine ethyl ester (3.85 g, 56%) as a colourless froth which did not crystallise.

(Found: C, 42.59; H, 3.54; N, 3.37; I, 31.61. $C_{28}H_{27}F_3I_2N_2O_6$. Requires: C, 42.12; H, 3.41; N, 3.51; I, 31.80%).

(g) This diiodo compound was treated with hydrobromic and acetic acids as described in Example 1(p) to give L-3,5-diiodo-3-[1-(6-oxo-3(1H)-pyridyl)-ethyl]-thyronine (2.14 g, 77%), m.p. 220°–230° (dec.).

EXAMPLE 10

L-3,5-Diiodo-O-methyl-3'-(6-oxo-3(1H)-pyridylmethyl)thyronine

A solution of L-3,5-diiodo-3'-(6-methoxy-3-pyridylmethyl)-O-methyl-N-trifluoroacetyl thyronine ethyl ester (1.90 g, prepared as in Example 2(d)) in glacial acetic acid (40 ml) and concentrated hydrochloric acid (40 ml) was refluxed with stirring for 17 hours. The solvents were evaporated and the resulting gum triturated with water. The mixture was cooled, the precipitate was collected and recrystallised several times from aqueous sodium hydroxide by addition of glacial acetic acid to pH approximately 6 to afford L-3,5-diiodo-O-methyl-3'-(6-oxo-3(1H)-pyridylmethyl)-thyronine as a light brown solid (1.02 g, 65%), m.p, 228° (dec.).

EXAMPLE 11

L-N-Acetyl-3,5-diiodo-3'-(6-oxo-3(1H)-pyridylmethyl)-thyronine

To a cooled (4°) solution of L-3,5-diiodo-3'-(6-oxo-(1H)-pyridylmethyl)-thyronine (0.90 g, prepared as in Example 2) in 2N sodium hydroxide (15 ml) was added acetic anhydride (0.68 ml). The solution was stirred at room temperature for 2 hours, with sufficient 2N sodium hydroxide periodically added to keep the solution basic. After acidification with concentrated hydrochloric acid and dilution with water (20 ml) the resulting precipitate was collected, washed with water then recrystallised twice from aqueous ethanolic sodium hydroxide on addition of glacial acetic acid to give L-N-acetyl-3,5-diiodo-3'-(6-oxo-3(1H)-pyridylmethyl)-thyronine as a grey coloured solid (0.72 g, 76%), m.p. 228°–231° (dec).

EXAMPLE 12

L-3,5-Dibromo-3'-(6-oxo-3(1H)-pyridylmethyl)-thyronine ethyl ester

L-3,5-Dibromo-3'-(6-oxo-3-(1H)-pyridylmethyl)-thyronine (4.0 g, prepared as described in Example 1)

was suspended in dry absolute ethanol (60 ml) and dry hydrogen chloride gas was passed for 3 hours. The solvents were evaporated and the residue was triturated with aqueous saturated sodium bicarbonate to give a white solid which was collected and chromatographed on silica gel. Elution with acetonitrile/ethanol 33% methylamine in ethanol (25:5:2) gave L-3,5-dibromo-3'-(6-oxo-3(1H)-pyridylmethyl)thyronine ethyl ester (3.0 g, 71%), m.p. 153°–55°.

EXAMPLE 13

L-3,5-Dibromo-3'-(6-oxo-3(1H)-pyridylmethyl)-thyroninamide

L-3,5-Dibromo-3'-(6-oxo-3(1H)-pyridylmethyl)-thyronine ethyl ester (2.0 g, prepared as described in Example 12) was dissolved in absolute alcohol (30 ml). Ammonia gas was passed through the solution for 2 hours, which was then heated in a bomb at 80° for a total of 7 hours. The reaction mixture was concentrated to give L-3,5-dibromo-3'-(6-oxo-3(1H)-pyridylmethyl)-thyroninamide (0.635 g, 39%), m.p. 238°–240° (dec.).

EXAMPLE 14

DL-4-(4'-Hydroxy-3'-(6-oxo-3(1H)-pyridylmethyl)-phenylthio)-3, 5-dichlorophenylalanine (a) To a stirred suspension of 2,6-dichloro-4-nitroaniline (200 g) in glacial acetic acid (1.3 l) at 16° was added dropwise a solution of sodium nitrite (93.84 g) in concentrated sulphuric acid (500 ml), keeping the reaction mixture below 22°. The reaction mixture was stirred and kept below this temperature for 0.5 hour, then poured slowly onto crushed ice/water (2.5 liters) containing urea (31.71 g), keeping the mixture below 23°. Potassium iodide (225.77 g) in water (600 ml) was slowly added with stirring and the mixture stirred at room temperature for 3 hours. The product was filtered off, washed with water then triturated with hot ethanol to give 3,5-dichloro-4-iodonitrobenzene (263.4 g, 86%) as a buff solid, m.p. 147°–150°.

(b) A solution of sodium hydroxide (5.80 g) in water (10 ml) was slowly added to a mixture of 3,5-dichloro-4-iodonitrobenzene (46.10 g) and 4-methoxy-3-(6-methoxy-3-thiophenol (38.00 g, prepared as in example 4 c) in 1,4-dioxan (100 ml), with stirring and the mixture was stirred for 20 minutes, then poured into water (300 ml) and extracted with chloroform (3 times).

The combined extracts were washed with water (3 times) then dried over anhydrous magnesium sulphate and evaporated to give an orange gum (66.88 g) which was chromatographed on silica gel using ethyl acetate-petroleum spirit (60°–80°, gradient elution) as eluant. 3,5-Dichloro-4-(4'-methoxy-3'-(6-methoxy-3-pyridylmethyl)phenylthio)-nitrobenzene was isolated as an orange solid (30.08 g, 46%), m.p. 115°–116° (from ethyl acetate-petroleum spirit (60–80) [1:4]).

(c) 3,5-Dichloro-4-(4'-methoxy-3'-(6-methoxy-3-pyridylmethyl)phenylthio)-nitrobenzene (28.60 g) and iron powder (35 g) were stirred with heating in glacial acetic acid (250 ml) at 90° for 40 minutes. The mixture was cooled, filtered, then evaporated to dryness and the resulting gum redissolved in chloroform, washed with water (twice), dried over anhydrous magnesium sulphate and evaporated to give the crude product as a light brown gum (27.17 g). This gum was chromatographed on silica gel using ethyl acetate-petroleum spirit (60°–80°, gradient elution) as eluant. 3,5-Dichloro-4-(4'-methoxy-3'-(6-methoxy-3-pyridylmethyl)phe-nylthio) aniline was isolated as a pale yellow solid (21.29 g, 79%), m.p. 114°–115°.

(d) A solution of sodium nitrite (2.19 g) in water (20 ml) was added dropwise to a cooled (10°) solution of 3,5-dichloro-4-(4'methoxy-3'-(6-methoxy-3-pyridylmethyl) phenylthio) aniline (8.94 g) in glacial acetic acid (50 ml) and concentrated sulphuric acid (2.6 ml) with stirring. After 10 minutes urea (1.0 g) was added and this cool solution added from a dropping funnel to a cooled (5°) suspension of cuprous cyanide (19.0 g) and sodium cyanide (10.4 g) in water (260 ml) keeping the temperature of the mixture below 10°. This mixture was stirred vigorously whilst allowing to warm to room temperature and then heated at 60° for 0.5 hour. After cooling chloroform (250 ml) and sodium acetate (10 g) were added. The organic layer was separated and the aqueous re-extracted with chloroform. The combined organic extracts were washed with water (four times), dried over anhydrous magnesium sulphate and evaporated to afford a red solid which was chromatographed on silica gel using ethyl acetate-petroleum spirit (60–80, gradient elution) as eluant. 3,5-Dichloro-4(4'-methoxy-3'-(6-methoxy-3-pyridylmethyl)phenylthio)benzonitrile was obtained as a pale yellow solid (4.20 g, 46%), m.p. 147°–150°.

(e) Diisobutylaluminium hydride (68.4 ml of a 1M hexane solution) was added dropwise to a stirred solution of 3,5-dichloro-4-(4'-methoxy-3'-(6-methoxy-pyridylmethyl) phenylthio)benzonitrile (7.36 g) in dry toluene (80 ml) at 50°, under a nitrogen atmosphere, and this reaction mixture was stirred at this temperature for 2.5 hours. The mixture was cooled and poured onto 2N HCl (250 ml) with vigorous stirring. After 20 minutes the organic layer was separated and the aqueous re-extracted with toluene. The organic extracts were combined, washed with water (three times), dried over anhydrous magnesium sulphate and evaporated to give an orange gum, which was purified by column chromatography on silica gel. 3,5-Dichloro-4-(4'-methoxy-3'-(6-methoxy-3-pyridylmethoxy)phenylthio)benzaldehyde was isolated, by elution with 10% ethyl acetate-petroleum spirit (60°–80°), as a pale yellow solid (3.00 g, 40%), m.p. 102°–104°.

(f) To a stirred solution of this aldehyde (2.62 g) in methanol (25 ml) and 1,4-dioxan (4 ml), cooled to 5°, was added sodium borohydride (0.46 g) in portions. The cooling bath was removed and the solution stirred for 0.5 hour. The solvents were evaporated and the residual grey gum dissolved in ethyl acetate, washed with water (three times), dried over anhydrous magnesium sulphate and evaporated to give 3,5-dichloro-4-(4'-methoxy-3'-(6-methoxy-3-pyridylmethyl)phenylthio-benzyl alcohol as a white solid (2.46 g, 93%), m.p. 115°–117°.

(g) To a cooled (−5°), stirred suspension of this benzyl alcohol (2.39 g) in dry dichloromethane (10 ml) was added triethylamine (1.25 ml) followed by toluene-4-sulphonylchloride (1.14 g) in portions. The reaction mixture was stirred whilst warming to 5° and stirred at this temperature for 1.5 hours. Water (30 ml) and chloroform (30 ml) were added and the organic layer was separated, washed with water (three times), dried over anhydrous magnesium sulphate and evaporated to give the crude tosylate as a yellow gum (3.06 g).

To a solution of sodium (0.110 g) in dry ethanol (20 ml), under nitrogen, was added diethylacetamidomalonate (1.04 g) and the clear solution was cooled to 5°. The crude tosylate (2.82 g, prepared above) in dry ethanol (20 ml), containing dry 1,4-dioxan (4 ml), was added from a dropping funnel. The reaction mixture was stirred whilst allowing to warm to room temperature and then stirred for 1 hour. Water (160 ml) and ethyl acetate (100 ml) were added and the organic layer separated. The aqueous was re-extracted with ethyl acetate and the organic layers were combined, washed with water (three times), dried over anhydrous magnesium sulphate and evaporated to give a yellow gum which was purified by exhaustive column chromatography on silica gel. N-Acetyl-3,5-dichloro-4-(4'-methoxy-3'-(6-methoxy-3-pyridylmethyl)phenylthio)-α-carbethoxy-phenylalanine ethyl ester was isolated by elution with toluene: glacial acetic acid (10:1) as a white solid (0.42 g, 13% from f), m.p. 170°–171°.

(h) To a cooled (−74°) solution of N-acetyl-3,5-dichloro-4-(4'-methoxy-3'-(6-methoxy-3-pyridylmethyl)phenylthio)-α-carbethoxy-phenylalanine ethly ester (0.39 g) in dry dichloromethane (10 ml) was added boron tribromide (0.58 ml) with stirring. The mixture was stirred whilst warming to room temperature and stirred for 5 hours. The reaction mixture was worked up and refluxed with concentrated hydrochloric in glacial acetic acid in a manner similar to that as described in Exampl 1 to afford DL-4-(4'-Hydroxy-3'-(6-oxo-3(1H)-pyridylmethyl) phenylthio)-3,5-dichlorophenylalanine as a cream solid (0.20 g, 70%), m.p. 261°–264°.

EXAMPLES 15–32

The following compounds were also prepared by the methods described above. All compounds had satisfactory elemental analyses and spectral data.

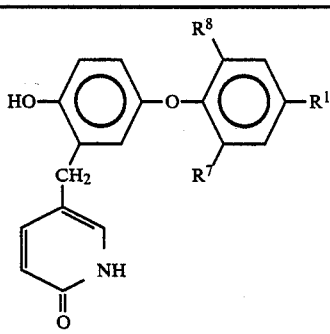

| Example | R¹ | R⁷ | R⁸ | m.p. |
|---|---|---|---|---|
| 15 | L-CH$_2$CH(NH$_2$)CO$_2$H | I | H | 227–30° (dec) |
| 16 | D-CH$_2$CH(NH$_2$)CO$_2$H | Br | Br | 259–60° (dec) |
| 17 | " | I | I | 245–8° (dec) |
| 18 | —CH$_2$CO$_2$H | Cl | Cl | 273–4° |
| 19 | " | Br | Br | 258–9° (dec) |
| 20 | " | I | I | 227–9° (dec) |
| 21 | —(CH$_2$)$_2$CO$_2$H | Cl | Cl | 250° (dec) |
| 22 | " | Br | Br | 276–7° (dec) |
| 23 | " | I | I | 175–6° |
| 24 | —(CH$_2$)$_3$CO$_2$H | Cl | Cl | 228–30° |
| 25 | " | Br | Br | 280–1° |
| 26 | " | I | I | 257° |
| 27 | —(CH$_2$)$_4$CO$_2$H | I | I | 249–53° |
| 28 | —(CH$_2$)$_2$NH$_2$.HCl | I | I | 209–10° |
| 29 | L-CH$_2$CH(NH$_2$)CO$_2$H | Br | NO$_2$ | 220° (dec) |
| 30 | " | I | Cl | 253–5° (dec) |
| 31 | L-CH$_2$CH(NH²)CO²Et | Cl | Cl | 100° (dec) |
| 32 | CO$_2$H | I | I | 277–84° (dec) |

Examples 15, 16 and 18–30 and 32 were prepared by reaction of the iodonium salts (prepared in Examples 1(d) and 1(e) with the appropriate phenol with R$_1$ in protected form (esterified and/or acylated) under the conditions of Example 1(g), followed by deprotection using the methods of Examples 1(h) and 1(p). Exmples 17, 19 and 20 were prepared by reaction the phenol of Example 1(l) with the appropriate R$_1$ protected (esterified and/or acylated) dinitrophenol under the conditions of Example 1(n), followed by conversion of the nitro groups to halogen as in Examples 1(o) and 2(d), then deprotection by the methods of Examples 1(h) and 1(p).

EXAMPLE 33

L-3,5-Dibromo-3'-(6-oxo-3(1H)-pyridazinylmethyl)-thyronine.

(a) o-Methoxyphenylacetonitrile (23.64 g) and 3,6-dichloropyridazine (23.93 g) were dissolved in dry dimethylformamide (50 ml) and sodium hydride (16.23 g of a 50% dispersion in oil) was slowly added in portions to the stirred solution over 2 hours. The mixture was poured on to excess crushed ice and extracted with dichloromethane. The organic layer was removed and washed with water, dried with anhydrous magnesium sulphate, charcoaled and evaporated to dryness. The residue crystallised from dichloromethane/petroleum spirit to give 1-(6-chloro-3-pyridazinyl)-1-(2-methoxyphenyl)-acetonitrile (35.5 g, 85%), m.p. 91°–92°

(b) This nitrile (33.5 g) was dissolved in concentrated hydrochloric acid (200 ml), acetic acid (100 ml) and water (100 ml) and the solution refluxed with stirring. After 6 hours the solvents were evaporated and the residue recrystallised from ethyl acetate/petroleum spirit to give 2-(6-oxo-3(1H)-pyridazinylmethyl)-anisole (21.4 g, 77%), m.p. 142°–3°.

(c) This pyridazinone (15.7 g) was dissolved in phosphorus oxychloride (22 ml) and the solution heated with stirring at 55° (oil bath) for 1 hour. The cooled mixture was slowly poured onto crushed ice, and extracted with dichloromethane. The organic layer was separated and washed with saturated sodium bicarbonate solution, dried with anhydrous magnesium sulphate and evaporated. The residue was combined with a smaller batch (from 2.16 g of the pyridazinone) and extracted several times with boiling petroleum spirit (60°–80°). The combined extracts were charcoaled and evaporated to give 2-(6-chloro-3-pyridazinylmethyl)-anisole (16.95 g, 87%), m.p. 63°.

(d) To a stirred suspension of iodine tristrifluoroacetate (prepared from 2.54 g of iodine as described in Example 1(e)) in trifluoroacetic anhydride (25 ml) at −15° was added the above chloropyridazine (9.39 g) in trifluoroacetic acid (20 ml) and trifluoroacetic anhydride (25 ml), keeping the temperature below −15°. The mixture was stirred at room temperature overnight, concentrated, then a solution of sodium acetate (25 g) and sodium perchlorate (15 g) in water (200 ml) was added. The mixture was extracted with chloroform, the organic solution dried with anhydrous magnesium sulphate, then concentrated to 50 ml and poured into stirred ether (250 ml). The precipitate was collected and dried to give crude 4,4'-dimethoxy-3,3'-bis-(6-chloro-3-pyridazinylmethyl)-diphenyl iodonium perchlorate (14 g). δ(DMSO-d$_6$) 3.80 (3H, s, —OCH$_3$), 4.20 (2H, s, —CH$_2$Ar), 7.05 (1H, m, Ar—5H̲), 7.65 (2H, m, PyH̲) and 8.00 (2H, m, Ar—2,6H̲).

(e) The above iodonium salt (12.45 g), L-3,5-dibromo-N-trifluoroacetyl tyrosine methyl ester (8.98 g, Example 1(f)), triethylamine (4.05 g) and copper bronze (1.0 g) were stirred in dichloromethane (50 ml) for 18 hours.

The mixture was filtered, washed with aqueous acetic acid, 2N sodium hydroxide, then water, then dried with anhydrous magnesium sulphate and evaporated. The residue was combined with a smaller batch (from 0.72 g of the iodonium salt) and purified by column chromatography on silica gel (400 g). Elution with ethyl acetate/petroleum spirit (60°–80°) [1:3] gave L-3,5-dibromo-3'-(6-chloro-3-pyridazinylmethyl)-O-methyl-N-trifluoroacetyl-thyronine methyl ester (4.0 g) as a tan coloured froth. $\delta$(CDCl$_3$) 3.06 (2H, m, ArC$\overline{H_2}$CH), 3.84 and 3.93 (6H, 2s,—OCH$_3$), 4.19(2H, s, $\overline{ArCH_2}$Py), 4.75(1H, m, ArCH$_2$C$\overline{H}$), 6.62 (3H, m, Ar$\underline{H}$ ), 7.17 (2H, m, Py$\underline{H}$) and 7.23 (2$\overline{H}$, s, Ar$\underline{H}$).

(f) The above dibromo compound (3.27 g) was dissolved in acetic acid (20 ml) containing sodium acetate (0.79 g). The solution was refluxed for 1.25 hours, sufficient water (approximately 2 ml) added to dissolve the precipitated sodium chloride, and the solution evaporated to dryness. The residue was partitioned between water and ethyl acetate, the organic layer removed and washed with saturated sodium bicarbonate, then dried with anhydrous magnesium sulphate and evaporated to dryness. The residue was crystallised from ethyl acetate/petroleum spirit (60°–80°) to give L-3,5-dibromo-O-methyl-3'-(6-oxo-3(1H)-pyridazinylmethyl)-N-trifluoroacetylthyronine methyl ester (2.52 g, 79%), m.p. 176°–8°.

(g) This pyridazinone (2.45 g) was dissolved in dry dichloromethane (40 ml) and cooled with stirring at 0°. Boron tribromide (6.46 g) in dichloromethane (3 ml) was added. A red-brown precipitate formed. The mixture was stirred at room temperature for 1.5 hours, then crushed ice was added. The mixture was filtered, the precipitate collected and dissolved in 2N sodium hydroxide (30 ml). The solution was heated on a steam bath for 15 minutes, acetic acid was then added to pH5, and the mixture cooled. The resulting precipitate was collected, washed and dried to give L-3,5-dibromo-3'-(6-oxo-3(1H)-pyridazinylmethyl)-thyronine (1.74 g, 88%), m.p. 278°–9° (dec.).

Alternatively, instead of using the perchlorate salt prepared in (d) for reaction step (e), the iodonium trifluoroacetate salt can be used, which is prepared as follows:

Iodine (159 g) was suspended in trifluoroacetic anhydride (1 liter) and stirred under nitrogen whilst fuming nitric acid (350 ml) was added over 1.5 hours, keeping the temperature between 36° and 40°. Trifluoroacetic anhydride (300 ml) was then added and the mixture maintained at 40° under a stream of nitrogen until all nitrogen oxides were removed, then allowed to stand at room temperature overnight. The solvent was then removed under reduced pressure and the residual solvent removed by azeotroping with trifluoroacetic anhydride (2×300 ml). The pale yellow residual solid was then suspended in trifluoroacetic anhydride (1.2 liters) with stirring and was cooled to −20°. A solution of 2-(6-chloro-3-pyridazinylmethyl)anisole (600 g) in trifluoroacetic acid (1.2 liters) was then added dropwise, maintaining the temperature between −10° and −20°. The mixture was stirred at −10° for 1 hour and at room temperature overnight, then the solvent removed under reduced pressure and the residue poured into a solution of sodium sulphate (3.5 kg) in water (20 liters) with stirring. The pH of this mixture was adjusted to approximately pH 2 using dilute aqueous sodium hydroxide, then extracted with dichloromethane (2×3 liters, 1×2 liters), the organic extracts combined, dried (MgSO$_4$), filtered, and reduced in volume to 2 liters, then added to vigorously stirred diethyl ether (12 liters). The dark grey precipitated solid was filtered off, washed with ether, and dried in a vacuum oven at 40° for 6 hours to give 4,4'-dimethoxy-3,3'-bis-(6-chloro-3-pyridazinylmethyl)diphenyl iodonium trifluoroacetate (814 g, 90%) m.p. 145°–147°.

Further reaction of this salt using procedures analogous to those described in 33(e), (f) and (g) above gives the required L-3,5-dibromo-3'-(6-oxo-3(1H)-pyridazinylmethyl)thyronine.

EXAMPLE 33A

L-3,5-Dibromo-3'-(6-oxo-3(1H)-pyridazinylmethyl)-thyronine (a) 2-(6-Chloro-3-pyridazinylmethyl)anisole (prepared as described in Example 33(c)) (2.35 g) was dissolved in dry dichloromethane (20 ml) and cooled with stirring to −50°. Boron tribromide (3 ml) was then added dropwise, and the solution was allowed to warm to room temperature. After 0.5 hours the orange reaction mixture was poured into ice/water (200 ml) and acetone added to dissolve the precipitated solid. The mixture was extracted with dichloromethane, the organic extracts were separated, washed with water, dried, and evaporated. The residue was recrystallised from ethyl acetate and petroleum spirit to give 2-(6-chloro-3-pyridazinylmethyl)phenol (1.75 g, 80%), m.p. 132°–132.5°.

Found: C, 59.61; H, 4.13; N, 12.47; Cl, 16.09;
C$_{11}$H$_9$ClN$_2$O.
Requires: C, 59.87; H, 4.11; N, 12.70; Cl, 16.07%.

(b) To a stirred solution of this phenol (2.4 g) and urea (14 g) in 75% aqueous sulphuric acid (100 ml) t-butanol (17 ml) was added slowly. The mixture was stirred well and further quantities of t-butanol were added after 4 hours (18 ml), 24 hours (5 ml), and 28 hours (20 ml). After 120 hours the mixture was poured into water, the organic phase separated and discarded and the aqueous phase extracted thoroughly with ether. The combined ether extracts were washed with saturated brine, then dried and evaporated. The residue was recrystallised from ether and petroleum spirit to give 2,4-di-t-butyl-6-(6-chloro-3-pyridazinylmethyl)phenol (3.43 g, 94%) m.p. 143.0°–143.5°.

Found: C, 68.32; H, 7.51; N, 8.36; Cl, 10.89;
C$_{19}$H$_{25}$ Cl N$_2$O.
Requires: C, 68.56; H, 7.57; N, 8.41; Cl, 10.65%).

(c) A solution of this phenol (1.95 g), L-3,5-dibromo-N-trifluoroacetyl tyrosine methyl ester (3.24 g) in diethyl ether (100 ml) was stirred under argon at room temperature and then treated with active manganese dioxide (3×5 g). After 4 hours the mixture was filtered, and titanium tetrachloride (5 ml) added. After 2 minutes the dark solution was treated with water and extracted well with ethyl acetate. The organic extracts were combined, washed with saturated brine, dried and evaporated. The residue was chromatographed on silica gel with petroleum spirit and ether as eluant to give L-3,5-dibromo-5'-t-butyl-3'-(6-chloro-3-pyridazinylmethyl)-N-trifluoroacetyl thyronine methyl ester (2.31 g, 55%), m.p. 84°–86°.

(d) A solution of this dibromothyronine (2.76 g) and anhydrous sodium acetate (0.78 g) in acetic acid (25 ml) was heated at reflux for 10 hours, then cooled and poured into ice-water. The precipitated solid was filtered off, dissolved in ethyl acetate, dried, and evaporated to give L-3,5-dibromo-5'-t-butyl-3'-(6-oxo-3(1H)-pyridazinylmethyl)-N-trifluoroacetylthyronine methyl ester, (2.4 g, 55%), m.p. 112°–115°.

(e) A solution of this pyridazinone (0.200 g) and HBr (1 ml) in glacial acetic acid (20 ml) was heated at reflux for three days. The solution was then cooled, diluted with water, basified with aqueous 2N sodium hydroxide solution and brought to pH 6 by addition of acetic acid. The precipitated solid was filtered, washed, and dried to give L-3,5-dibromo-3'-(6-oxo-3(1H)-pyridazinylmethyl)thyronine (0.100 g, 65%) m.p. 245.247° (dec.), spectroscopically identical with that previously isolated (Example 33(g)).

EXAMPLE 33B

L-3,5-Dibromo-3'-(6-oxo-3(1H)-pyridazinylmethyl)-thyronine (a) To a solution of iodine tristrifluoroacetate (prepared by treatment of iodine (10.0 g) with fuming nitric acid (20.95 ml) in acetic anhydride and trifluoroacetic acid) in acetic anhydride (50 ml), cooled to −10°, was added dropwise a solution of 2-methoxybenzyl cyanide (30.0 g) in trifluoroacetic acid (60 ml) and acetic anhydride (30 ml). The temperature of the mixture was maintained below 0° during the addition then allowed to stand at room temperature overnight. The mixture was then poured into a well-stirred ice-cold solution of sodium acetate (100 g) and sodium perchlorate (13.0 g) in water (600 ml). The solid which precipitated was filtered off, washed with water and diethyl ether to give 3,3'-dicyanomethyl-4,4'-dimethoxy-diphenyl iodonium perchlorate as a fine buff solid (23.6 g, 57%), m.p. 183°–4° (from methanol/diethyl ether).

(b) A solution of this iodonium salt (22.6 g), L-3,5-dibromo-N-trifluoroacetyltyrosine methyl ester (Example 1(f)), triethylamine (6.1 g) in dichloromethane (300 ml) was treated with copper bronze (1 g) and the mixture stirred at room temperature for 20 hours. The mixture was then filtered and the filtrate washed with 2N aqueous hydrochloric acid (2×200 ml), water (2×200 ml), and 2N aqueous sodium hydroxide solution (3×200 ml), then the organic solution was dried over magnesium sulphate and evaporated under reduced pressure. The oily residue was dissolved in dichloromethane (30 ml) and poured into petroleum spirit. A solid precipitated which was filtered off and recrystallised from dichloromerthane/petroleum spirit to give L-3,5-dibromo-3'-cyanomethyl-O-methyl-N-trifluoroacetyl-thyronine methyl ester as a colourless crystalline solid, m.p. 148°–149°. The mother liquors were chromatographed on silica gel to give further quantities of this compound (total=8.05 g, 31%).

(c) To a solution of this dibromothyronine (120 mg) and 3,6-dichloropyridazine (31 mg) in dry dimethylformamide (2 ml), sodium hydride (30 mg of a 50% suspension in oil) was added and the reaction mixture allowed to stand at room temperature for 50 min. It was then treated with ice, and the aqueous mixture extracted with dichloromethane, the organic solution washed with saturated brine, then dried and evaporated. The residue was chromatographed on a preparative silica gel chromatography plate from which 3,5-dibromo-3'-(1-(6-chloro-3-pyridazinyl)-1-cyanomethyl)-O-methyl-N-trifluoroactylthyronine methyl ester (5 mg) was isolated. δ(CDCl$_3$) 3.12 (1H, m), 3.27 (1H, m), 3.79 (3H, s), 3.86 (3H, s), 4.86 (1H, m), 5.80 (1H, s), 6.72 (1H, dd), 6.83 (1H, d), 7.04 (1H, d), 7.15 (1H, broad m), 7.37 (2H, s), 7.50 (2H, dd).

Elaboration of this intermediate by standard methods gives the title compound.

EXAMPLE 34

L-3,5-Diiodo-3'-(6-oxo-3(1H)-pyridazinylmethyl)-thyronine (a) 5-Benzyloxy-2-methoxybenzaldehyde (150.4 g) was suspended in methanol (600 ml) and to the gently warmed stirred mixture was added, in portions, sodium borohydride (15.0 g). The methanol was evaporated and the reidue partitioned between dichloromethane and water. The organic layer was washed with water, then saturated sodium chloride, dried with anhydrous magnesium sulphate and evaporated to dryness. The residue crystallised from dichloromethane/petroleum spirit (40°–60°) to give 5-benzyloxy-2-methoxybenzyl alcohol (143.8 g, 95%), m.p. 50°–51°.

(b) The above benzyl alcohol (143.8 g) was dissolved in dry dichloromethane and to the stirred cooled (−5°) solution was added, dropwise, a solution of phosphorus tribromide (58.5 g) in dichloromethane (100 ml), keeping the temperature below 0°. Additional dichloromethane (100 ml) was added to facilitate stirring. The mixture was stirred to 10°, water (500 ml) was added, the organic layer separated, thoroughly washed with water, dried with anhydrous magnesium sulphate and evaporated to dryness. The residue was recrystallised from dichloromethane/petroleum spirit (60°–80°) to give 5-benyloxy-2-methoxy-benzyl bromide (146.8 g, 81%), m.p. 88°–90°.

(c) Sodium cyanide (16.12 g) was dissolved in hot dimethyl sulphoxide (250 ml). To the warm solution was added, in portions with stirring, the above benzyl bromide (100 g); a precipitate appeared. The cooled solid mass was treated with excess water (total volume 1.21), the mixture stirred vigorously, the precipitate collected and recrystallised from methanol on addition of water to give 5-benzyloxy-2-methoxyphenyl acetonitrile (72.2 g, 87%), m.p. 63°–5°.

(d) The above nitrile (14.84 g) was treated with 3,6-dichloropyridazine and sodium hydride as described in Example 33(a) to give 1-(5-benzyloxy-2-methoxyphenyl)-1-(6-chloro-3-pyridazinyl)-acetonitrile (13.8 g, 64%), m.p. 152°–6° (dec.) (from chloroform/petrol).

(e) The above chloropyridazine (12.83 g) was dissolved in acetic acid (70 ml) containing sodium acetate (5.76 g). The solution was refluxed 1 hour, and to the hot mixture was added water (70 ml). The mixture was cooled, the precipitate collected and washed and dried to give 1-(5-benzyloxy-2-methoxyphenyl)-1-(6-oxo-3(1H)-pyridazinyl)-acetonitrile (11.43 g, 94%), m.p. 194°–5°.

(f) The above nitrile (11.00 g) was dissolved in concentrated hydrochloric acid (50 ml) and acetic acid (100 ml) and the mixture refluxed for 20 minutes, then evaporated to dryness. The residue was dissolved in concentrated hydrochloric acid (50 ml) and water (50 ml) and refluxed with stirring for 6 hours. Trituration of the cooled solution gave 4-methoxy-3-(6-oxo-3(1H)-pyridazinylmethyl)-phenol hydrochloride (2.36 g), m.p. 175°–82°. A second crop of the product (4.6 g, total yield 82%) was obtained upon concentration of the mother liquors.

(g) The above phenol (6.94 g) was treated with L-3,5-dinitro-N-trifluoroacetyl-tyrosine ethyl ester (Example 1(m) as described in Example 1(n) to give L-3,5-dinitro-O-methyl-3'-(6-oxo-3(1H)-pyridazinylmethyl)-N-trifluoroacetyl thyronine ethyl ester (6.56 g, 36%), m.p. 170°-2° (from ethyl acetate/petroleum spirit (60°-80°)).

(h) The dinitro compound obtained above was successively reduced, bis-diazotised and iodinated as described in Example 2(d) to give, after purification by column chromatography and recrystallisation from aqueous ethanol, L-3,5-diiodo-O-methyl-3'-(6-oxo-3(1H)-pyridazinylmethyl)-N-trifluoroacetyl thyronine ethyl ester (2.00 g, 24%), m.p. 220°-3° (dec.).

(i) The preceding diiodo compound (1.82 g) was treated with boron tribromide, then with sodium hydroxide as described in Example 33(g) to give L-3,5-diiodo-3'-(6-oxo-3(1H)-pyridazinylmethyl)-thyronine (1.00 g, 67%), m.p. 258°-62° (dec.).

EXAMPLE 35

L-3,5-Dichloro-3'-(6-oxo-3(1H)-pyridazinylmethyl)-thyronine (a) Reaction of L-3,5-dichloro-N-trifluoroacetyl tyrosine methyl ester (Example 3(a)) with the iodonium perchlorate of Example 33(d) was carried out as described in Example 33(e). The product was treated with sodium acetate in acetic acid as described in Example 33(f) to give L-3,5-dichloro-O-methyl-3'-(6-oxo-3(1H)-pyridazinylmethyl)-N-trifluoroacetyl-thyronine methyl ester, m.p. 157°-60° (from ethyl acetate/petroleum spirit (60°-80°)).

(b) The dichloro compound (1.04 g) was treated with boron tribromide followed by sodium hydroxide as described in Example 33(g) to give L-3,5-dichloro-3'-(6-oxo-3(1H)-pyridazinylmethyl)-thyronine (0.69 g, 85%), m.p. 245° (dec.).

EXAMPLE 36

L-3,5-Diiodo-3'-(5-hydroxy-2-pyridylmethyl)-thyronine (a) 2-Amino-5-methoxypyridine (14.8 g, prepared by the method of J. G. Lombardino, *J. Med. Chem.*, 1981, 24, 39) was dissolved in 60% hydrobromic acid (150 ml) and to the cooled ($-10°$) stirred solution bromine (47.47 g) was added dropwise. To the resulting yellow suspension was added, dropwise, sodium nitrite (20.53 g) in water (40 ml), keeping the temperature below $-5°$. The mixture was stirred to room temperature, and after 0.5 hour cooled to 0°, and a solution of sodium hydroxide (120 g) in water (100 ml) was slowly added. The mixture was thoroughly extracted with ether, the combined ether extracts dried with anhydrous sodium sulphate, and evaporated. The residue was chromatographed on silica gel (150 g). Elution with dichloromethane gave a yellow oil (14.1 g, 63%) which was combined with a smaller batch (3.4 g) and distilled under reduced pressure to give 2-bromo-5-methoxypyridine (16.4 g). b.p. 76°-78°/0.6 torr.

(b) 2-Bromo-5-methoxypyridine (15.35 g) was successively treated with n-butyl lithium and 5-benzyloxy-2-methoxybenzaldehyde (16.47 g, Example 1(i)) under the conditions of Example 1(j). The crude carbinol (19.4 g) was treated with acetic anhydride and pyridine as described in Example 1(k). The product was purified by column chromatography on silica gel (550 g). Elution with petroleum spirit (60°-80°)/ethyl acetate (2:1), then recrystallisation from dichloromethane/petroleum spirit gave 1-(3-benzyloxy-6-methoxyphenyl)-1-(5-methoxy-2-pyridyl)-methyl acetate (13.29 g, 50%), m.p. 105°-110°.

(c) The acetate (11.78 g) was hydrogenated in glacial acetic acid (60 ml) and concentrated hydrochloric acid (0.5 ml) with 10% palladium on charcoal (3.0 g). When hydrogen uptake had ceased, the mixture was filtered, evaporated to dryness, and partitioned between chloroform and saturated potassium bicarbonate solution. The organic layer was separated, dried with anhydrous sodium sulphate and evaporated to dryness. The residue was triturated with petroleum spirit/ether to give 4-methoxy-3-(5-methoxy-2-pyridylmethyl)-phenol (4.72 g, 64%), m.p. 115°-22°.

(d) The preceding phenol was treated with L-3,5-dinitro-N-trifluoroacetyl-tyrosine ethyl ester (Example 1(m)) as described in Example 1(n) to give L-3,5-dinitro-3'-(5-methoxy-2-pyridylmethyl)-O-methyl-N-trifluoroacetyl thyronine ethyl ester (8.04 g, 68%) as a yellow froth after column chromatography.

(Found: C, 51.89; H, 4.13; N, 8.47. $C_{27}H_{25}F_3N_4O_{10}$. Requires: C, 52.09; H, 4.05; N, 9.00%);.

(e) The dinitro compound (7.70 g) was successively reduced, bis-diazotised and iodinated as described in Example 2(d). Purification by exhaustive medium pressure column chromatography gave L-3,5-diiodo-3'-(5-methoxy-2-pyridylmethyl)-O-methyl-N-trifluoroacetyl thyronine ethyl ester (0.85 g, 9%), m.p. 108°-10° (from aqueous ethanol).

(f) The diiodo compound (0.72 g) was dissolved in dichloromethane (10 ml) and added dropwise to a cooled (0°) stirred solution of boron tribromide (27.6 g) and dichloromethane (4 ml); a brown precipitate formed. The mixture was stirred at room temperature for 17 hours, diluted with dichloromethane (50 ml) and cautiously added to stirred ice/water (300 ml). The pH of the aqueous mixture was adjusted to 4 and the mixture thoroughly extracted with ethyl acetate. The combined organic extracts were evaporated to dryness and dissolved in 2N sodium hydroxide (20 ml) and water (30 ml). The solution was heated on a steam bath for 10 minutes, charcoaled, filtered, and treated with acetic acid to pH5. The precipitate was collected, washed and dried to give L-3,5-diiodo-3'-(5-hydroxy-2-pyridylmethyl)-thyronine (0.43 g, 74%), m.p. 277° (dec.).

EXAMPLE 37

L-3,5-Diiodo-3'-(4-hydroxybenzyl)-thyronine (a) 2,4'-Dimethoxydiphenylmethane (103 g, prepared by the method of A. M. Choudhury et. al., *J. Chem. Soc. C.*, 1970, 2543) in trifluoroacetic acid (70 ml) and acetic anhydride (150 ml) was added during 1 hour to a stirred suspension of iodine tris-trifluoroacetate (105 g) in acetic anhydride (150 ml) at 18°-20°. After 40 minutes the solvents were evaporated, the residue dissolved in methanol (150 ml) and poured into a stirred solution of potassium bromide (150 g) in water (600 ml). The solid precipitate was collected and dried to give crude 4,4'-dimethoxy-3,3'-bis-(4-methoxybenzyl)-diphenyl iodonium bromide (56 g, 37%), m.p. 110° (dec.).

(b) The preceding iodonium bromide (25 g), L-3,5-diiodo-N-trifluoroacetyl tyrosine methyl ester (20.52 g, Example 2(a)), triethylamine (12 ml) and copper bronze (1 g) were stirred in methanol at room temperature for 19 hours. The mixture was filtered, evaporated to dryness, redissolved in toluene, and washed successively with 1N potassium hydroxide and water. The organic solution was dried with anhydrous magnesium sulphate and evaporated to dryness. The residue was purified by column chromatography on silica gel, eluting with chloroform to give L-3,5-diiodo-3'-(4-methoxybenzyl)-O-methyl-N-trifluoroacetyl thyronine methyl ester (3.51 g, 12%). m.p. 89°–92° (from chloroform/petroleum spirit).

(c) The diiodo compound (3.37 g) was treated successively with boron tribromide and sodium hydroxide as described in Example 33(g) to give L-3,5diiodo-3'-(4hydroxybenzyl)thyronine (1.3 g, 64%), m.p. 251°–3°.

Alternatively, the title compound was prepared as follows:

(d) To the Grignard reagent prepared from 4-bromoanisole (286 g) and magnesium turnings (38.5 g) in dry tetrahydrofuran (480 ml) was added, dropwise, with vigorous stirring, a solution of 5-hydroxy-2-methoxybenzaldehyde (100 g) in dry tetrahydrofuran (1 liter). The mixture was heated on a steam bath for 3 hours, cooled and decomposed with saturated ammonium chloride solution. The organic layer was removed and the aqueous extracted with ethyl acetate (twice). The combined organics were washed with water, dried with anhydrous magnesium sulphate and evaporated to dryness. The residue was stirred with water (4 liters), and the buff coloured solid collected and dried to give crude 1-(5-hydroxy-2-methoxyphenyl)-1-(4-methoxyphenyl)-methanol (170 g, 99%), m.p. 62°–68°. This carbinol (85 g) was dissolved in ethanol (700 ml) and 10% palladium on charcoal (10 g) added. The mixture was hydrogenated in a Parr apparatus at 45° until hydrogen uptake ceased. The mixture was filtered, the filtrate evaporated to dryness and the residue filtered through a column containing silica gel, eluting with dichloromethane, to give 2,4'-dimethoxy-5-hydroxydiphenylmethane (46 g, 58%), m.p. 56°–58° (from petroleum spirit (60°–80°)).

(e) The phenol obtained above was treated with L-3,5-dinitro-N-trifluoroacetyl tyrosine ethyl ester (Example 1(m)) as described in Example 1(n) and the resulting dinitro thyronine (m.p. 98°–100°) converted to the diiodo compound (m.p. 94°–7°) as described in Example 2(d). Deprotection of this diiodo compound as described in Example 33(g) gave L-3,5-diiodo-3'-(4-hydroxybenzyl)thyronine, identical in all respects to the sample obtained in (c) above.

EXAMPLE 38

L-3,5-Diiodo-4-(4'-hydroxy-3'-(4-hydroxybenzyl)-phenylthio)-phenylalanine (a) Treatment of 2,4'-dimethoxydiphenylmethane with lead thiocyanate and chlorine as described in Example 4(a) gave 2,4'-dimethoxy-5-thiocyanodiphenylmethane as an oil which did not crystallise.
(Found: C, 67.16; H, 5.31; N, 5.01; S, 10.91. $C_{15}H_{15}NO_2S$. Requires: C, 67.34; H, 5.30; N, 4.91; S, 11.21%).

(b) A solution of the thiocyanate (40.82 g) and sodium hydroxide (21 g) in water (120 ml) and dioxan (120 ml) was refluxed under nitrogen for 7 hours. The mixture was cooled, acidified to pH3 with concentrated hydrochloric acid, and extracted with chloroform. The organic solution was dried with anhydrous magnesium sulphate and evaporated to give the disulphide which was dissolved in acetic acid (150 ml) and concentrated hydrochloric acid (15 ml). Powdered zinc (23 g) was added and the mixture refluxed with stirring for 2 hours. The mixture was filtered, diluted with water (11), extracted with chloroform and the organic solution dried with anhydrous magnesium sulphate and evaporated to give 4-methoxy-3-(4-methoxybenzyl)-thiophenol (36.3 g, 97%), m.p. 78°.

(c) The thiophenol was reacted with L-3,5-dinitro-N-trifluoroacetyl tyrosine (Example 1(m)) as described in Example 4(d) to give L-3,5-dinitro-4-(4'-methoxy-3'-(4-methoxybezyl)-phenylthio)-N-trifluoroacetyl phenylalanine ethyl ester (73%), m.p. 100°–110° (from ether/petroleum spirit).

(d) The dinitro compound (5.0 g) was reduced, bisdiazotised and iodinated as described in Example 4(e). Exhaustive purification by column chromatography on silica gel gave L-3,5-diiodo-4-(4'-methoxy-3'-(4-methoxybenzyl)phenylthio)-N-trifluoroacetyl phenylalanine ethyl ester (2.7 g), m.p. 122°–3°.

(e) The diiodo compound (2.2 g) was treated successively with boron tribromide then sodium hydroxide as described in Example 33(g) to give L-3,5-diiodo-4-(4'-hydroxy-3'-(4-hydroxybenzyl)-phenylthio)-phenylalanine (1.45 g), m.p. 281°–2°.

EXAMPLE 39

L-3,5-Diiodo-3'-(1-(4-hydroxyphenyl)-ethyl)-thyronine (a) To a stirred solution of the Grignard reagent prepared from 4-bromoanisole (29.58 g) and magnesium turnings (3.89 g) in tetrahydrofuran (90 ml) was added 5-benzyloxy-2-methoxyacetophenone (16.21 g, Example 9(g)) in dry tetrahydrofuran (120 ml) at 20° over 3 hours. After 1 hour saturated ammonium chloride solution (200 ml) was added, the organic layer was removed, and the aqueous extracted with ethyl acetate. The combined organics were dried with anhydrous sodium sulphate and evaporated to dryness. The residue was extracted with boiling petroleum spirit (60°–80°, 3×200 ml) and on cooling 1-(5-benzyloxy-2-methoxyphenyl)-1-(4-methoxyphenyl)ethanol (12.19 g, 53%) was obtained, m.p. 97°–100°.

(b) A suspension of the carbinol (12.04 g) in ethanol (75 ml) containing 10% palladium on charcoal (1.0 g) was hydrogenated on a Parr apparatus. When uptake of hydrogen was complete, the mixture was filtered, evaporated to dryness, and the residue triturated with dichloromethane/petroleum spirit (60°–80°) to give 4-methoxy-5-(1-(4-methoxyphenyl)ethyl)phenol (7.12 g, 85%), m.p. 81°–83°.

(c) This phenol (8.40 g) was reacted with L-3,5-dinitro-N-trifluoroacetyl tyrosine ethyl ester (Example 1(m)) as described in Example 1(n). Purification of the product by chromatography on silica gel, eluting with chloroform, gave L-3,5-dinitro-3'-(1-(4-methoxyphenyl)-ethyl-O-methyl-N-trifluoroacetyl thyronine ethyl ester (9.6 g, 45%) as a non crystalline glass.
(Found: C, 53.76; H, 4.44; N, 6.14. $C_{29}H_{28}F_3N_3O_{10}$. Requires: C, 54.80; H, 4.44; N, 6.61%).

(d) The dinitro compound (9.2 g) was reduced, bisdiazotised and iodinated as described in Example 2(d). The crude product (4.84 g), obtained after column chromatography on silica gel, was dissolved in dry dichloromethane (70 ml) and treated with boron tribromide as described in Example 1(h). The product was purified by column chromatography on silica gel, (230 g), eluting with toluene/acetone (8:1) to give L-3,5-diiodo-3'-(1-(4-hydroxyphenyl)-ethyl)-N-trifluoroacetyl thyronine ethyl ester (1.62 g), m.p. 128°–138°.

(e) The diiodo phenol obtained above (1.48 g) was dissolved in ethanol (6 ml) and a solution of sodium hydroxide (0.50 g) in water (1 ml) was added. The solution was kept at room temperature for 2 hours, filtered, heated on a steam bath for 10 minutes, and the hot solution adjusted to pH approximately 5 with glacial acetic acid. Water was added (total volume 100 ml) and on cooling a precipitate formed which was collected and washed to give L-3,5-diiodo-3'-(1-(4-hydroxyphenyl)ethyl)thyronine (0.80 g, 65%), m.p. 204°–8°.

Also prepared by the methods described above were:

EXAMPLE 40

L-N-Acetyl-3,5-diiodo-3'-(4-hydroxybenzyl)-thyronine, m.p. 133°–135°.

EXAMPLE 41

Sodium 3,5-dibromo-3'-(6-oxo-3(1H)-pyridazinylmethyl) thyroethanoate, m.p. 205°–207° (dec).

EXAMPLE 42

D-3,5-Dibromo-3'-(6-oxo-3(1H)-pyridazinylmethyl)-thyronine, m.p. 253°–255°.

EXAMPLE 43

DL-3,5-Dibromo-3'-(6-oxo-3(1H)-pyridazinylmethyl)-α-methyl thyronine, m.p. 288° (decomp).

Found: C, 44.63; H, 3.45; N, 7.41; Cl, 28.74, $C_{21}H_{19}Br_2N_3O_5.0.6H_2O$. Requires: C, 44.77; H, 3.60; N, 7.46; Cl, 28.37%).

EXAMPLE 44

DL-3,5-Dibromo-3'-(6-oxo-3(1H)-pyridazinylmethyl)-thyronine (a) (i) 3,5-Dibromo-4-iodobenzonitrile (m.p. 170°–175°) was prepared from 4-amino-3,5-dibromobenzonitrile by the method described in Example 14(a).

(ii) 4-Methoxy-3-(6-oxo-3(1H)-pyridazinylmethyl)-phenol was precipitated from an aqueous solution of crude 4-methoxy-3-(6-oxo-3(1H)-pyridazinylmethyl)-phenol hydrochloride (Example 34(f)). It was then washed and dried to give a buff solid, m.p. 95°–98°.

(iii) This phenol (2.55 g) was added to a stirred suspension of sodium hydride (1.00 g of a 50% dispersion in oil) in dry dimethylformamide at 40°. The mixture was then cooled to room temperature, 3,5-dibromo-4-iodobenzonitrile (4.00 g) added and the reaction mixture stirred at 60° for 1.5 hours, when it was cooled and poured into water. The aqueous mixture was then extracted with ethyl acetate, the organic extracts combined and washed with water, dried and evaporated to give a brown oil which solidified on trituration with dichloromethane and petroleum spirit. This solid was recrystallised from methanol/water to give 3,5-dibromo-4-(4-methoxy-3-(6-oxo-3(1H)-pyridazinylmethyl)phenoxy)benzonitrile (2.53 g, 46.5%) m.p. 214°–216°.

(iv) To a solution of this nitrile (0.50 g) in dry dichloromethane (10 ml) cooled to −70° was added to a solution of diisobutylaluminium hydride in toluene (3 ml, 25% w:w solution), and the resulting mixture stirred for 45 minutes. It was then poured into ice-cold 2N aqueous hydrochloric acid with vigorous stirring. After 20 minutes, chloroform (50 ml) was added and the mixture filtered to remove insoluble material. The phases were extracted twice with chloroform, the organic extracts combined, washed with water, dried and evaporated. The residue was chromatographed on silica gel with toluene and acetic acid (25:1) as eluants. The fractions were evaporated to dryness, azetroped with water and the residue recrystallised from ethyl acetate/petroleum spirit to give 3,5-dibromo-4-(4-methoxy-3-(6-oxo-3(1H)-pyridazinylmethyl)phenoxy)benzaldehyde (0.21 g, 42%), m.p. 183°–184°.

(iv) A solution of this benzaldehyde (0.35 g), anhydrous sodium acetate (0.09 g), and N-acetylglycine (0.13 g) in acetic anhydride (5 ml) was stirred at 100° under nitrogen for 19 hours. The dark brown solution was then evaporated to dryness and triturated with water to give a light brown solid. This solid was treated with 2N aqueous sodium hydroxide (5 ml) and ethanol (10 ml) at 50° for 30 minutes. The mixture was then cooled and brought to pH 6 by addition of glacial acetic acid. The solution was concentrated to remove ethanol, diluted with water and extracted with ethyl acetate. The organic extract were combined, washed with water, then dried and evaporated to dryness. The residue was chromatographed on silica gel, with chloroform/glacial acetic acid (20:1) as eluant, to give α-acetamido-β-(3,5-dibromo-4-(4-methoxy-3-(6-oxo-3(1H)-pyridazinylmethyl)phenoxy)phenyl-1-propenoic acid as a buff-coloured solid (0.120 g, 30%), m.p. 240°–243°.

Elaboration of this intermediate (or alternatively the intermediate product of (iii)) by standard methods gives the title compound.

(b) Methane sulphonyl chloride (3.6 g) was added to a solution of 3-bromo-4-hydroxy-5-nitrobenzaldehyde (7.7 g) in dry pyridine (100 ml), and the mixture heated at reflux for 10 min. A solution of 4-methoxy-3-(6-oxo-3(1H)pyridazinylmethyl)phenol (prepared as in Example 44(a)) (6.6 g) in dry pyridine (50 ml) was then added and the resultant dark mixture heated at reflx for 1.5 hours, then allowed to cool to room temperature. The solvent was then evaporated and the residue dissolved in dichloromethane (150 ml), washed with aqueous 2N hydrochloride acid (100 ml), water (100 ml), aqueous saturated sodium bicarbonate solution (2×100 ml) and water (4×100 ml), then dried and evaporated to dryness. The orange residue was dissolved in IMS, treated with charcoal and filtered. On addition of water (200 ml) and cooling a precipitate was formed which was filtered off and dried. This solid was recrystallised from ethyl acetate/petroleum spirit to give 3-bromo-5-nitro-4-(4-methoxy-3-(6-oxo-3(1H)-pyridazinylmethyl)-phenoxy)benzaldehyde (5.2 g, 40%) as a yellow solid, m.p. 188°–190°.

Elaboration of this intermediate by standard methods gives the title compound.

The structures of the compounds synthesised in Examples 33–44 are given below.

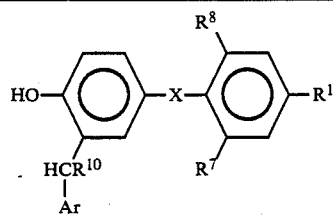

| Example | Ar | R¹ | R⁷=R⁸ | X | R¹⁰ |
|---|---|---|---|---|---|
| 33 | (4-oxo-1,2-dihydropyridazin-3-yl) | L—CH$_2$CH(NH$_2$)CO$_2$H | Br | O | H |
| 34 | " | " | I | O | H |
| 35 | " | " | Cl | O | H |
| 36 | (pyridin-N, 4-OH) | " | I | O | H |
| 37 | (phenyl-4-OH) | " | I | O | H |
| 38 | " | " | I | S | H |
| 39 | " | " | I | O | CH$_3$ |
| 40 | " | L—CH$_2$CH(NHCOCH$_3$)CO$_2$H | I | O | H |
| 41 | (4-oxo-1,2-dihydropyridazin-3-yl) | —CH$_2$CO$_2$Na | Br | O | H |
| 42 | " | D—CH$_2$CH(NH$_2$)CO$_2$H | Br | O | H |
| 43 | " | DL—CH$_2$C(CH$_3$)(NH$_2$)CO$_2$H | Br | O | H |
| 44 | " | DL—CH$_2$CH(NH$_2$)CO$_2$H | Br | O | H |

EXAMPLE A

A syrup formulation for oral administration is prepared from

| | |
|---|---|
| Compound of Example 33 | 10 mg |
| Propylene glycol | 10 g |
| Methyl parahydroxybenzoate | 0.1 g |
| Propyl parahydroxybenzoate | 20 mg |
| Sorbitol solution (70% w:v) | 20 ml |
| Flavours | 0.5 mg |
| Saccharin Sodium | 5.0 mg |
| Water | to 100 ml | by dissolving the active ingredient and preservatives in the propylene glycol, adding the sorbitol, flavours, sweeteners, mixing, and adjusting the volume to 100 ml with water.

EXAMPLE B

A solution for injection (0.5 mg/ml) is prepared from

| | |
|---|---|
| Compound of Example 33 | 50 mg |
| sodium hydroxide (0.1 N) | 4 ml |
| Hydrochloric acid (0.1 N) | to pH 10 |
| Sodium chloride | 0.9 g |
| Water | to 100 ml |

The active ingredient is dissolved in the sodium hydroxide, the volume adjusted to 80–90 ml with water and the pH adjusted to 10 by dropwise addition of the hydrochloric acid. Finally the sodium chloride is added, the volume adjusted to 100 ml with water and the filtered solution filled into ampoules or vials. The final product can be sterlised by filteration or by autoclave.

EXAMPLE C

A 0.1 mg tablet for oral administration is prepared from the following:

| | mg/tablet |
|---|---|
| Compound of Example 33 | 0.1 |
| Microcrystalline cellulose | 81.9 |
| Sodium Starch glycollate | 4 |
| Lactose | 45 |
| Magnesirm Stearate | 1 |
| [Film coat (colour & polymers) | 3] |

The active ingredient is milled and mixed with the microcrystalline cellulose, sodium starch glycollate and lactose in a suitable blender. The magnesium stearate is added, the mixture blended to obtain uniformity and the mixture compressed into a tablet. Optionally the tablet is then provided with the aqueous film coating containing colour.

EXAMPLE D

A suppository for rectal administration is prepared by forming a melt of the compound of Example 33 (100 mg) and suppocire A.M. (1900 mg), pouring the molten mass into suitable moulds and allowing to cool.

BIOLOGICAL DATA (a) Dosing Solutions

Compounds of structure (I) were dissolved in the minimum possible volume of N NaOH and diluted in 0.01M NaOH/0.154M NaCl or 50% polyethylene glycol (Koch-Light; MW=400) in distilled water. Final concentrations gave the required dose/kg in 1 ml for i.m. injection and in 5 ml for oral dosing.

(b) Mitochondrial α-Glycerophosphate Dehydrogenase (GPDH; EC 1.1.9 9.5) Measurement The activity of GPDH in 100 ul aliquots of diluted tissue homogenates was determined at 37° according to the method of Fried, G. H., Greenberg, N. and Antopol, W., (Proc. Soc. Exp. Biol. Med. 1961, 107, 523–5). In this assay GPDH was used to catalyse the reduction by sn-glycerol-phosphate of 2-p-iodo-3-nitro-5-phenyl tetrazolium chloride (I.N.T.) to the corresponding formazan. The formazan was extracted with ethyl acetate and its absorbence determined at 490 nm. The activity of each tissue was measured in duplicate at two dilutions and corrected for non-specific reduction of I.N.T. found in the absence of sn-glycerol-3-phosphate.

(c) Metabolic Rate

Metabolic rate was measured by a calibrated, pressure-activated device which delivered small, known volumes of oxygen to a rat in a closed chamber containing soda lime to absorb expired $CO_2$. The temperature was maintained at 29±0.3°. Alternatively, the depression of oxygen concentration in air flowing through an animal chamber at a known rate is used as a measure of oxygen consumption by the animal.

(d) Effect on Plasma Cholesterol

Total plasma cholesterol levels were determined by the use of a cholesterol oxidase kit, for example the Merck CHOD Iodide colourimetric kit.

(e) Effect on Plasma Triglyceride Levels

Plasma triglyceride levels were measured using enzymatic colour tests (Merck System GPO-PAP method).

RESULTS (i) Effect on GPDH Levels and Metabolic Rate

After 7 daily oral or intramuscular doses of between 0.1 to 50 mg/kg, the compounds of Examples 1 to 4, 8, 12, 16 to 18, 20, 25, 33 to 38 and 42 were found to have raised the basal metabolic rate of euthyroid rats by around 20%, and raised hepatic GPDH levels by between 3 to 5 fold without significant effect on cardiac GPDH levels. No significant toxic side-effects were observed during these tests.

(ii) Effect on Total Plasma Cholesterol and Triglyceride Levels

The compound of example 1 namely, L-3,5-dibromo-3'-(6-oxo-3(1H)-pyridylmethyl)-thyronine reduced dog plasma total cholesterol levels by up to 42% and raised metabolic rate by 10 to 20% without affecting heart rate after 7 daily i.v. doses of 1 to 10 mg/kg.

The compound of example 3 namely, L-3,5-dichloro-3'-(6-oxo-3(1H)-pyridylmethyl)-thyronine reduced dog plasma total cholesterol levels by up to 55% without affecting metabolic rate or heart rate after 7 daily i.v. doses of 8.5 mg/kg.

The compound of example 33 namely, L-3,5-dibromo-3'-(6-oxo-3(1H)-pyridazinylmethyl)-thyronine:

(a) reduced serum total cholesterol of euthyroid cats by 40% after 7 daily i.v. doses of 0.1 mg/kg, without affecting metabolic rate or heart rate. In the same experiment the compound lowered LDL cholesterol and the ratio of LDL to HDL cholesterol;

(b) had no effect on heart rate or metabolic rate of hypothyroid rats after 7 daily i.m. doses of 0.02 mg/kg;

(c) reduced total plasma cholesterol of cholesterol fed euthyroid rats by 13% after 7 daily oral doses of 0.01 mg/kg; and, by 28% after 7 daily oral doses of 0.1 mg/kg;

(d) reduced plasma total cholesterol of cholesterol fed hypothyroid rats by 60% after 14 daily oral doses of 0.01 mg/kg;

(e) reduced plasma triglyceride concentrations of cholesterol fed euthyroid rats by 71% after 21 daily oral doses of 0.1 mg/kg;

(f) reduced plasma triglyceride concentrations of normal diet fed euthyroid rats by 71% after 21 daily oral doses of 1 mg/kg;

(g) reduced plasma triglyceride concentrations of cholesterol fed hypothyroid rats by 73% after 21 daily oral doses of 0.1 mg/kg.

The effect of a number of consecutive daily oral doses of the compounds of examples 2, 20, 34, 36, 37 and 42 on total plasma cholesterol of cholesterol fed hypothyroid rats is given in the following Table:

| Example No. | Daily Oral Dose mg/kg | No. of Days | % reduction in total plasma cholesterol |
|---|---|---|---|
| 2 | 0.10 | 7 | 64 |
| 20 | 0.01 | 14 | 27 |
| 34 | 0.10 | 7 | 74 |
| 36 | 0.01 | 7 | 68 |
| 37 | 0.10 | 7 | 60 |
| 42 | 0.01 | 7 | 83 |

No overt signs of toxicity were observed in any of the foregoing tests.

What is claimed is:

1. A compound of structure (I)

$$\begin{array}{c} R^9 \underset{HCR^{10}}{\underset{|}{\bigcirc}} X \underset{R^7}{\overset{R^8}{\bigcirc}} R^1 \\ Ar \end{array} \quad (I)$$

in which,
$R^1$ is $-CH_2CR^2R^3NR^4R^5$ or $YCOR^6$;
$R^2$ is hydrogen or $C_{1-4}$alkyl;
$R^3$ is hydrogen or $-COR^6$;
$R^4$ is hydrogen or $C_{1-4}$alkyl;
$R^5$ is hydrogen, $C_{1-4}$alkyl or $C_{1-4}$alkanoyl;

$R^6$ is hydroxy, $C_{1-4}$alkoxy, or $-NR^4R^5$;

Y is a bond or $C_{1-4}$alkylene;

$R^7$ and $R^8$ are the same or different and are each hydrogen, halogen, $C_{1-4}$alkyl, nitro or amino, X is oxygen, sulphur or $CH_2$;

$R^9$ is hydroxy or $C_{1-4}$alkoxy, aryl $C_{1-4}$alkoxy, $C_{1-4}$alkanoyloxy, aryl $C_{1-4}$alkanoyloxy, arylsulphonyloxy, alkylsulphonyloxy, or O-glucuronide;

$R^{10}$ is hydrogen or $C_{1-4}$alkyl; and

Ar is 4-hydroxyphenyl, or a pharmaceutically acceptable salt thereof.

2. A compound as claimed in claim 1 in which $R^1$ is

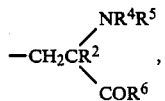

and $R^2$, $R^4$, $R^5$ and $R^6$ are as defined in claim 1.

3. A pharmaceutical composition having selective thyromimetic activity comprising a compound as claimed in claim 1, in association with a pharmaceutically acceptable carrier.

4. A method of producing selective thyromimetic activity in certain tissues except the heart which comprises administering to an animal in need thereof an effective amount to produce said activity of a compound as claimed in claim 1.

5. A method of lowering plasma lipid levels which comprises administering to an animal in need thereof an effective amount to produce said activity of a compound as claimed in claim 1.

6. A method of lowering the ratio of LDL-cholesterol to HDL-cholesterol which comprises administering to an animal in need thereof an effective amount to produce said activity of a compound as claimed in claim 1.

7. A compound of claim 1 which is L-3,5-diiodo-3,'-(4-hydroxybenzyl)-thyronine.

8. A compound of claim 1 which is L-3,5-diiodo-4-(4,'-hydroxy-3,'-(4-hydroxybenzyl)-phenylthio)-phenylalanine.

9. A compound of claim 1 which is L-3,5-diiodo-3,'-(1-(4-hydroxypehnyl)-ethyl)-thyronine.

10. A compound of claim 1 which is L-N-acetyl-3,5-diiodo-3,'-(4-hydroxybenzyl)-thyronine.

* * * * *